United States Patent
Sawyer et al.

(10) Patent No.: US 12,035,718 B2
(45) Date of Patent: *Jul. 16, 2024

(54) BIOFILM PENETRATING COMPOSITIONS AND METHODS

(71) Applicant: Nevada Naturals Inc., Albuquerque, NM (US)

(72) Inventors: Anthony J. Sawyer, Albuquerque, NM (US); Richard F. Stockel, Bridgewater, NJ (US)

(73) Assignee: Nevada Naturals Inc., Albuquerque, NM (US)

( * ) Notice: Subject to any disclaimer, the term of this patent is extended or adjusted under 35 U.S.C. 154(b) by 112 days.

This patent is subject to a terminal disclaimer.

(21) Appl. No.: 17/457,186

(22) Filed: Dec. 1, 2021

(65) Prior Publication Data

US 2022/0117230 A1 Apr. 21, 2022

Related U.S. Application Data

(60) Division of application No. 16/950,350, filed on Nov. 17, 2020, now Pat. No. 11,191,274, which is a continuation of application No. 16/703,397, filed on Dec. 4, 2019, now Pat. No. 10,849,324, which is a division of application No. 15/966,088, filed on Apr. 30, 2018, now abandoned.

(60) Provisional application No. 62/492,131, filed on Apr. 29, 2017.

(51) Int. Cl.
| | |
|---|---|
| A01N 47/44 | (2006.01) |
| A01N 37/36 | (2006.01) |
| A01N 43/16 | (2006.01) |
| A61L 15/20 | (2006.01) |
| A61L 15/46 | (2006.01) |
| A61L 15/60 | (2006.01) |
| A61L 17/00 | (2006.01) |
| A61L 26/00 | (2006.01) |
| A61L 27/34 | (2006.01) |
| A61L 27/52 | (2006.01) |
| A61L 27/54 | (2006.01) |
| A61L 29/08 | (2006.01) |
| A61L 29/14 | (2006.01) |
| A61L 29/16 | (2006.01) |
| A61L 31/10 | (2006.01) |
| A61L 31/14 | (2006.01) |
| A61L 31/16 | (2006.01) |

(52) U.S. Cl.
CPC ............ *A01N 47/44* (2013.01); *A01N 37/36* (2013.01); *A01N 43/16* (2013.01); *A61L 15/20* (2013.01); *A61L 15/46* (2013.01); *A61L 15/60* (2013.01); *A61L 17/005* (2013.01); *A61L 27/34* (2013.01); *A61L 27/52* (2013.01); *A61L 27/54* (2013.01); *A61L 29/085* (2013.01); *A61L 29/145* (2013.01); *A61L 29/16* (2013.01); *A61L 31/10* (2013.01); *A61L 31/145* (2013.01); *A61L 31/16* (2013.01); *A01N 2300/00* (2013.01); *A61L 26/0066* (2013.01); *A61L 2300/406* (2013.01); *A61L 2400/04* (2013.01)

(58) Field of Classification Search
CPC ........ A01N 37/36; A01N 43/16; A01N 47/44; A01N 2300/00; A61L 15/20; A61L 15/46; A61L 15/60; A61L 17/005; A61L 26/0066; A61L 27/34; A61L 27/52; A61L 27/54; A61L 29/085; A61L 29/145; A61L 29/16; A61L 31/10; A61L 31/145; A61L 31/16; A61L 2300/406; A61L 2400/04

See application file for complete search history.

(56) References Cited

U.S. PATENT DOCUMENTS

| | | | |
|---|---|---|---|
| 4,002,775 | A | 1/1977 | Kabara |
| 5,284,833 | A | 2/1994 | McAnalley et al. |
| 6,417,144 | B2 | 7/2002 | Tsuzuki et al. |
| 6,468,551 | B1 | 10/2002 | Diec et al. |
| 7,597,903 | B2 | 10/2009 | Rosinskaya et al. |
| 7,662,417 | B2 | 2/2010 | Bonaventurea et al. |
| 8,193,244 | B1 | 6/2012 | Stockel et al. |

(Continued)

FOREIGN PATENT DOCUMENTS

WO 2012013577 A1 2/2012

OTHER PUBLICATIONS

Krausslich et al., Antiviral Strategies, Handbook of Experimental Pharmacology, 2009, Springer-Verlag Berlin Heidelberg, p. 1-24. (Year: 2009).*

(Continued)

*Primary Examiner* — Jonathan S Lau
(74) *Attorney, Agent, or Firm* — BENESCH, FRIEDLANDER, COPLAN & ARONOFF LLP

(57) ABSTRACT

Compositions are provided that have at least two of three active ingredients. The active ingredients maybe a salt having a cation $N^\alpha$ C8-C16 alkanoyl-L di-basic amino acid —C1-C4 alkyl ester, a glycerol monoester of a fatty acid and a sugar ester of a fatty acid. The compositions are useful in methods of killing or inhibiting planktonic bacteria or fungi and bacteria or fungi embedded in a biofilm and prevention of biofilm formation on surfaces. The composition may further comprise a hydrogel and a benefit agent such as an antibiotic that can be solubilized by the hydrogel and supplied to the biofilm matrix by the active ingredients of the composition. Devices such as chronic wound coverings coated with the composition are also provided. Methods of preserving products with the composition are also provided.

11 Claims, 7 Drawing Sheets

(56) References Cited

U.S. PATENT DOCUMENTS

| | | | |
|---|---|---|---|
| 8,388,986 | B2 | 3/2013 | Urgell Beltran et al. |
| 8,513,305 | B2 | 8/2013 | Davies |
| 8,604,073 | B2 | 12/2013 | Ming et al. |
| 8,829,053 | B2 | 9/2014 | Salamone et al. |
| 8,932,624 | B2 | 1/2015 | Modak et al. |
| 9,283,278 | B2 | 3/2016 | Rodeheaver et al. |
| 9,763,453 | B2 | 9/2017 | Cook et al. |
| 2002/0165168 | A1 | 11/2002 | Bunger et al. |
| 2005/0031551 | A1 | 2/2005 | Prencipe |
| 2006/0105025 | A1 | 5/2006 | Hill et al. |
| 2007/0116750 | A1 | 5/2007 | Wolcott |
| 2008/0063693 | A1 | 3/2008 | Cook et al. |
| 2010/0330136 | A1 | 12/2010 | Rocabayera Bonvila |
| 2014/0314873 | A1 | 10/2014 | Beal et al. |
| 2015/0087582 | A1 | 3/2015 | LoVetri et al. |
| 2015/0098910 | A1 | 4/2015 | Mordas et al. |
| 2016/0128932 | A1 | 5/2016 | DuBourdieu et al. |
| 2017/0042916 | A1 | 2/2017 | Hilliard et al. |
| 2017/0360825 | A1 | 12/2017 | Salamone et al. |
| 2018/0078642 | A1 | 3/2018 | Cox et al. |

OTHER PUBLICATIONS

Raja et al., Plos One, 2017, 12(3), e0174024, 41 pages, published Mar. 20, 2017. (Year: 2017).*

Furukawa et al., International Journal of Food Microbiology, 2010, 138, p. 176-180. (Year: 2010).*

Kim et al., Journal of Membrane Science, 2016, 507, p. 24-33. (Year: 2016).*

S. Jeong et al., "Testing the influence of surfactant-based wound dressings on proteinase activity", International Wound Journal ISSN 1742-4801, pp. 1-5.

D. Davies et al., "A Fatty Acid Messenger is Responsible for Inducing Dispersion in Microbial Biofilms", Journal of Bacteriology, Vo. 191, No. 5, Mar. 2009, p. 1393-1403.

V. Braun et al., "The Tricky Ways Bacteria Cope with Iron Limitation", Iron Uptake in Bacteria with Emphasis on *E. coli* and *Pseudomonas*, Chapter 2, 2013, pp. 31-66.

D. Musk et al., "Iron Salts Perturb Biofilm Formation and Disrupt Existing Biofilms of Pseudomonas aeruginosa", Chemistry & Biology, vol. 12, 789-796, Jul. 2005, pp. 789-796.

Y. Ham et al., "Inhibitory activity of monoacylglycerols on biofilm formation in Aeromonas hydrophila, *Streptococcus mutans, Xanthomonas oryzae*, and *Yersinia enterocolitica*", SpringerPlus (2016) 5:1526, 8 pgs.

S. N. Kłodzińska et al., "Inhalable Antimicrobials for Treatment of Bacterial Biofilm-Associated Sinusitis in Cystic Fibrosis Patients: Challenges and Drug Delivery Approaches", International Journal of Molecular Sciences, Oct. 9, 2016, 19 pgs.

J. D. Bryers, Medical Biofilms, Biotechnol Bioeng., May 1, 2008, pp. 1-18.

P. M. Schlievert et al., "Glycerol Monolaurate Antibacterial Activity in Broth and Biofilm Cultures", PLoS ONE, vol. 7, Issue 7, Jul. 2012, pp. 1-12.

S. Furukawa et al., "Sugar fatty acid esters inhibit biofilm formation by food-borne pathogenic bacteria", Int J Food Microbiol. Mar. 31, 2010; 138(1-2), pp. 176-180.

General and Plastic Surgery Devices Panel of the Medical Devices Advisory Committee, "Classification of Wound Dressings Combined with Drugs" Clinical Discussion, Sep. 20-21, 2016, 141 pgs. "Biofilms provide added level of AM resistance", FDA Committee, 2 pgs.

M. Sadekuzzaman et al., "Evaluation of a novel antimicrobial (lauric arginate ester) substance against biofilm of *Escherichia coli* O157:H7, *Listeria monocytogenes*, and *Salmonella* spp.", International Journal of Food Science and Technology 2017, 52, pp. 2058-2067.

K. Chen, "Chemically induced biofilm detachment", Montana State University, Apr. 1998, 128 pgs.

D.D. Rhoads et al., "Biofilms in wounds: management strategies", Journal of Wound Care, vol. 17, No. 11, Nov. 2008, pp. 502-508.

R.D. Wolcott et al., "Biofilms and chronic wound inflammation", Journal of Wound Care, vol. 17, No. 8, Aug. 2008, pp. 333-341.

Phillips et al., "Biofilms made easy", Wounds International 2010, vol. 1, Issue 3, May 2010, 6 pgs.

D. J. Hess et al., "Antibacterial Synergy of Glycerol Monolaurate and Aminoglycosides in *Staphylococcus aureus* Biofilms", Antimicrobial Agents and Chemotherapy, vol. 58, No. 11, Nov. 11, pp. 6970-6973/.

K. L. Strandberg et al., "Glycerol Monolaurate Inhibits Candida and Gardnerella vaginalis In Vitro and In Vivo but Not Lactobacillus", Antimicrobial Agents and Chemotherapy, vol. 54, No. 2, Feb. 2010, pp. 597-601.

Z. He et al., "Anti-biofilm Activities from Resveratrol against Fusobacterium nucleatum", Frontiers in Microbiology, vol. 7, Jul. 2016, pp. 1-9.

C. Zambori et al., "Biofilm Implication in Oral Diseases of Dogs and Cats", Scientific Papers: Animal Science and Biotechnologies, 2012, 45, pp. 208-212.

Q. Yang et al., "A surfactant-based wound dressing can reduce bacterial biofilms in a porcine skin explant model", International Wound Journal ISSN 1742-4801, 2016, pp. 1-6.

D. Machado et al., "Bacterial Vaginosis Biofilms: Challenges to Current Therapies and Emerging Solutions", Frontiers in Microbiology, vol. 6, Article 1528, Jan. 2016, pp. 1-13.

K. Lester, "Zoocin A and lauricidin in combination selectively inhibit *Streptococcus* mutans in a biofilm model", University of Otago, Dunedin, New Zealand, Nov. 2010, 236 pgs.

G. Rodeheaver, "Structure and Properties of PluroGel®: A New Surfactant-based Biomaterial", PluroGen Therapeutics, 2016, pp. 2-4.

E. P. Orringer et al., "Purified Poloxamer 188 for Treatment of Acute Vaso-occlusive Crisis of Sickle Cell Disease", JAMA, vol. 286, No. 17, Nov. 7, 2001, pp. 2099-2106.

P. L. Phillips et al., "Antimicrobial dressing efficacy against mature Pseudomonas aeruginosa biofilm on porcine skin explants", International Wound Journal ISSN 1742-4801, 2013, pp. 1-15.

N. Barraud et al., "Involvement of Nitric Oxide in Biofilm Dispersal of Pseudomonas aeruginosa", Journal of Bacteriology, vol. 188, No. 21, Nov. 2006, pp. 7344-7353.

J. H. Fastenberg et al., "Biofilms in chronic rhinosinusitis: Pathophysiology and therapeutic strategies", World Journal of Otorhinolaryngology-Head and Neck Surgery, 2016, 219-229.

E. A. Mueller et al., "Non-Aqueous Glycerol Monolaurate Gel Exhibits Antibacterial and Anti-Biofilm Activity against Gram-Positive and Gram-Negative Pathogens", Plos One, Mar. 23, 2015, pp. 1-12.

Y. Ham et al., "Inhibitory activity of monoacylglycerols on biofilm formation in Aeromonas hydrophila, *Streptococcus mutans* , Xanthomonas oryzae, and Yersinia enterocolitica", SpringerPlus, 2016, 8 pgs.

D. Gil et al., "Novel Antibacterial Coating on Orthopedic Wires to Eliminate Pin Tract Infections", Antimicrobial Agents and Chemotherapy, vol. 61, Iss. 7, Jul. 2017, pp. 1-14.

H. Tyner et al., "Propionibacterium acnes biofilm e A sanctuary for *Staphylococcus aureus*?", Anaerobe 40, 2016, pp. 63-67.

J. D. Mhatre et al., "Comparative study on cytotoxicity activity of N-$\alpha$-acylarginine ethyl ester", International Letters of Chemistry, Physics and Astronomy, 8(1), 2013, pp. 1-7.

A. Gamarra-Montes et al., "Antibacterial Films Made of Ionic Complexes of Poly(-glutamic acid) and Ethyl Lauroyl Arginate", Polymers, 2018, 14 pgs.

T. Kim et al., "Lauroyl Arginate Ethyl Blocks the Iron Signals Necessary for Pseudomonas aeruginosa Biofilm Development", Frontiers in Microbiology, vol. 8, Article 970, May 2017, 11 pgs.

J. J. Kabara et al., "Fatty Acids and Derivatives as Antimicrobial Agents", Antimicrobial Agents and Chemotherapy, vol. 2, No. 1, pp. 23-28.

Cruces et al., "Improved Synthesis of Sucrose Fatty Acid Monoesters", JAOCS, 2001, 78(5), p. 541-546, 2001.

Entry for 1-Monolaurin, PubChem website, https://pubchem.ncbi.nlm.nih.gov/compound/14871, accessed on line on Aug. 28, 2019.

(56) References Cited

OTHER PUBLICATIONS

PreInterview First Office Action issued in U.S. Appl. No. 16/703,397, dated May 28, 2020.
Hayes, M.L., "The Effects of Fatty Acids and Their Monoesters on the Metabolic Activity of Dental Plaque",J. Dent. Res., 1984, 63(1), p. 2-5, (Year: 1984).
First Action Interview issued in U.S. Appl. No. 16/950,350, dated Mar. 23, 2021.
Dusane, et al., "Disruption of fungal and bacterial biofilms by lauroyl glucose", Letters in Applied Microbiology, 2008, 47, p. 374-379. (Year: 2008).
Seleem, et al., "In vitro evaluation of antifungal activity of monolaurin against Candida albicans biofilms", PeerJ 4: e2148; DIU 10.7717/peerj.2148. (Year: 2016).
Kelkar, et al., "Hydrocarbon emulsification and enhanced crude oil degradation by lauroyl glucose ester", Bioresource Technology, 2007, 98, p. 1505-1508 (Year: 2007).
Ferrer et al., "Synthesis of sugar esters in solvent mixtures by lipases from Thermomyces lanuginosus and Candida antarctica B, and their antimicrobial properties", Enzyme and Microbial Technology, 2005, 36, p. 391-398. Year: 2005).
Pre-Interview First Office Action issued in U.S. Appl. No. 16/950,350, dated Feb. 3, 2021.

\* cited by examiner

The formulations tested in Example 1.

| Formulation | LAB-HCl | ML | SL | HPC | TEC | Low MWt Dextrin | CDM | Propylene Glycol | Distilled Water | Avg. Log reduction |
|---|---|---|---|---|---|---|---|---|---|---|
| #1 | 0.8g | 0.5g | 1.0g | 2.3g | 0.5g | | | 20g | 80g | 5 |
| #2 | 0.8g | 0.5g | 1.0g | 2.3g | 0.5g | 2g | | 20g | 80g | 7 |
| #3 | 0.8g | 0.5g | 1.0g | 2.3g | 0.5g | | | 20g | 80g | >2 |
| #4 | 0.8g | 0.5g | 1.0g | 2.3g | | 2g | 1g | 20g | 80g | >4 |

A bar chart of the log CFUs remaining after the treatment.

The formulations tested in Example 2.

| Formulation | LAE-HCl | ML | SL | HPC | TEC | Propylene Glycol | Distilled Water | Avg. Log reduction |
|---|---|---|---|---|---|---|---|---|
| R-170131-1 | 1.0g | 0.5g | 10g | 2.2g | 1g | 20g | 80g | <1 |
| R-170201-2 | 1.0g |  | 10g | 2.2g | 1g | 20g | 80g | <2 |
| R-170202-3 | 1.0g |  | 10g | 2.2g | 1g | 25g | 75g | >3 |
| R-170203-4 | 2.0g | 2g | 6g | 2.2g | 1g | 25g | 75g | >4 |
| R-170204-5 | 1.0g | 2g | 6g | 2.2g | 1g | 25g | 75g | <3 |
| R-170205-6 | 1.0g | 0.5g | 3g | 2.2g | 1g | 30g | 70g | >4 |

A bar chart of the log CFUs remaining after the treatment.

The formulations tested in Example 3.

| Formulation | LAE | ML | SL | HPC | TEC | PG | Distilled Water | Avg Log reduction |
|---|---|---|---|---|---|---|---|---|
| R-17031-1 | 2g | 2g | 6g | 2.3g | 1g | 25g | 75g | >2 |
| R-17031-2 | 2g | 2g | 10g | 2.3g | 1g | 30g | 70g | >3 |
| R-17031-3 | 2g | 2g | 10g | 2.3g | 1g | 35g | 65g | >7 |
| R-17031-4 | 2g | 2g | 10g | 2.3g | 1g | 40g | 60g | Complete elimination |

A bar chart of the log CFUs remaining after the treatment.

The formulations tested in Example 4.

| Formulation | LAE | ML | SL | HPCadded at end | TECBuffer | PG | Distilled Water | Polaxamer188 | Avg Log reduction |
|---|---|---|---|---|---|---|---|---|---|
| A | 2g | 2g | 10g | 2.2g | 1g | 40g | 60g | | 9 |
| B | 2g | --- | 10g | 2.2g | 1g | 40g | 60g | | Complete elimination |
| C | --- | 2g | 10g | 2.2g | 1g | 40g | 60g | | 9 |
| D | 2g | 2g | 10g | | 1g | 40g | 60g | | Complete elimination |
| E | 2g | 2g | 10g | | 1g | 40g | 10g | 50g | 4 |
| F | 2g | 2g | 10g | | 1g | 40g | 10g | 50g | 4 |
| G | 2g | 2g | --- | 2.2g | 1g | 40g | 60g | | 6 |

A bar chart of the log CFUs remaining after the treatment.

The formulations tested in Example 5.

| Sample | LAE.-HCl | ML | SL | HPC | NaNO3 | PG | Water | Log reduction |
|---|---|---|---|---|---|---|---|---|
| #1 | 0.2g | --- | 0.4g | 2.2g |  | 25g | 75g | A:>4 B:5 |
| #2 | --- | 0.2g | 0.4g | 2.2g |  | 40g | 75g | A:>6 B:>6 |
| #3 | 0.2g | 0.2g | 0.4g | 2.2g |  | 35g | 65g | A:>4 B:>6 |
| #4 | 0.2g | 0.2g | 0.4g | 2.2g | 0.4g | 35g | 75g | A:4 B:>4 |

Time kill testing

| SL/ML ratio, wt/wt | S.aureus CFU | Log.CFU | AvgLogreduction |
|---|---|---|---|
| 0%SL/0%ML | $1.66 \times 10^7$ | 7.2g | NA |
| 100%SL/0%ML | $1.02 \times 10^7$ | 7g | 0.1 |
| 75%SL/25%ML | $4.80 \times 10^6$ | 6.65g | 0.65 |
| 50%SL/50%ML | $5.80 \times 10^4$ | 4.75g | 2.6 |
| 25%SL/75% | $1.76 \times 10^5$ | 5.25g | 1.8 |
| 100%ML/0%SL | $6.50 \times 10^4$ | 4.85g | 2.45 |

FIG. 6A

Table 6B

| SL/ML ratio, wt/wt | C.albicans, MIC (ppm) |
|---|---|
| 0%SL/100%ML | 12-25 |
| 25%SL/75%ML | 25-50 |
| 50%SL/50%ML | 25-50 |
| 75%SL/25%ML | 25-50 |
| 100%SL/0%ML | >200 |

FIG. 6B

| SL/LAE ratio, wt/wt | Ratio SL to LAE | C.albicans, MIC(ppm) | Synergy (enhancement) |
|---|---|---|---|
| 67%SL/33%LAE | 2 to 1 | 5-100 | Yes |
| 33%SL/67%LAE | 1 to 2 | 5-100 | Yes |
| 0%SL/100%LAE | NA | 5-100 | NA |

FIG. 7

| SL/LAE ratio, wt/wt | C.albicans, MIC(ppm) | S.Aureus MIC(ppm) |
|---|---|---|
| 0%SL/100%LAE | 12-25 | 16 |
| 25%SL/75%LAE | 25-50 | 23 |
| 50%SL/50%LAE | 25-50 | 23 |
| 75%SL/25%LAE | 25-50 | 23 |
| 100%SL/0%LAE | >500 | >500 |

FIG. 8A

| SL/LAE ratio, wt/wt | S.epidermidis MIC(ppm) |
|---|---|
| 0%SL/100%LAE | 15 |
| 40%SL/60%LAE | 9 |
| 50%SL/50%LAE | 8 |
| 60%SL/40%LAE | 6 |
| 100%SL/0%LAE | >500 |

FIG. 8B

BIOFILM PENETRATING COMPOSITIONS AND METHODS

PRIORITY

This application is a divisional of U.S. patent application Ser. No. 16/950,350 filed Nov. 17, 2020, now U.S. Pat. No. 11,191,274 issued Dec. 7, 2021, which is a continuation of U.S. patent application Ser. No. 16/703,391, filed Dec. 4, 2019, now U.S. Pat. No. 10,849,324 issued Dec. 1, 2020, which is a divisional of U.S. patent application Ser. No. 15/966,088, filed Apr. 3, 2018, now abandoned, which claims priority to U.S. Provisional Pat. App. No. 62/492,131, filed on Apr. 29, 2017, which are incorporated by reference herein in its entirety.

BACKGROUND

Previous patents WO 2013/169231 A1, U.S. Pat. Nos. 9,023,891, 9,271,495, 8,834,857, 8,926,997, 8,795,638, 8,734,879 and 8,193,244 have disclosed salts having a cation $N^\alpha$ C8-C16 alkanoyl-L di-basic amino acid —C1-C4 alkyl ester and various anions selected from the group consisting of halide, nitrite, nitrate, phenolate, polyphenolate, carboxylate, hydroxycarboxylate, hyaluronate, antibiotic anion and an amino acid.

U.S. Pat. No. 8,604,073 disclose medical devices incorporated with a biofilm inhibiting composition that comprises lauric arginate (LAE) and an antibiotic. U.S. Pat. No. 8,604,073 discloses an antimicrobial composition comprising lauric arginate (LAE) and one or more antibiotic.

Gil et al. (Antimicrobial Agents and Chemotherapy, July 2017 Vol. 61 Is. 7) report the use of monolaurin stainless steel K-wires were coated with monolaurin solubilized in ethanol using a simple but effective dip-coating method.

LAE has been disclosed as inhibiting biofilm formation on surgical implants and catheters (WO2012013577). U.S. Pub. Appl. No. 2015/0010715 discloses antimicrobial coatings are composed of a hydrogel and a bioactive agent including a substantially water-insoluble antimicrobial metallic material (silver sulfadiazine) that is solubilized within the coating. U.S. Pat. No. 6,638,978 lists a preservative formulation for food and cosmetics consisting of glyceryl mono-laurate (monolaurin, or "ML"), a mixture of caprylic and capric acid and propylene glycol in an aqueous base.

U.S. Pat. No. 4,002,775 discloses the discovery that highly effective and yet food-grade microbicides are provided by mono-esters of a polyol and a twelve-carbon atom aliphatic carboxylic fatty acid.

Biofilm

It is accepted that biofilms are a ubiquitous problem in industry, dentistry and medicine (Rhoads et al., J. of Wound Care, Vol. 17, No. 11, November 2008). Phillips et al. (Wounds International, Vol 1, Issue 3 May 2010) described biofilms as complex microbial communities containing bacteria and fungi (yeast and molds). The microorganisms synthesize and secrete a protective matrix that attaches the biofilm firmly to a living or non-living surface. Biofilms are dynamic heterogeneous communities that are continuously changing. At the most basic level a biofilm can be described as bacteria or fungi embedded in a thick, barrier of sugars and proteins. The biofilm barrier protects the microorganisms from external threats. Biofilms have long been known to form on surfaces of medical devices, such as urinary catheters, endotracheal and tympanostomy tubes, orthopedic and breast implants, contact lenses, intrauterine devices (IUDs) and sutures. They are a major contributor to diseases that are characterized by an underlying bacterial infection and chronic inflammation, e.g. periodontal disease, cystic fibrosis, chronic acne and osteomyelitis. Kaplan, et al. (J. of Bact. December 2004, p. 8213-8220) write that the extracellular polymeric substances (EPS) matrix may also contribute to the increased resistance to antibiotics and host defenses exhibited by biofilm cells. Polysaccharide is a major component of the EPS matrix in most bacterial biofilms.

A serious potential problem not addressed by many wound healing techniques is the presence of biofilms, particularly biofilms containing *Pseudomonas aeruginosa* (*P. aeruginosa* or *Pseudomonas a.* or *Pseudomans a.*). The microbial cells growing in a biofilm are physiologically distinct from planktonic cells of the same organism, which by contrast are single-cells that may float or move in a liquid medium. When a cell switches to the biofilm mode of growth, it undergoes a phenotypic shift in behavior in which large suites of genes are differentially regulated. A critical factor in the development of biofilm is that a specific type of signal molecule by microorganisms is important for the switching on and off of various properties such as virulence factor and biofilm production. This type of property is called quorum sensing.

Wounds, Burns, and Biofilm

Biofilm is a very serious problem and is responsible for persistent infections when treating burn wounds or wounds in general (Costertan et al., Science 284: p 1318-1322 (1999)). It is suggested that biofilms contain anoxic regions where the metabolic activity and also the susceptibility to antimicrobials of aerobes such as *P. aeruginosa* is reduced (Walters et al, Antimicrob. Agents Chemother, 47: p 317-323 (2003).

Livestock and Companion Animals

It has been reported that biofilm formation by bacterial pathogens of veterinary or zoonotic importance has surprisingly received relatively little attention. For example, animals have problems with plaque biofilm formation on their teeth. Publications have reported that chew toys as well as water bowls are a source of biofilm that results from the saliva enzymes. Biofilm bacteria can also cause systemic inflammation, cardiovascular diseases, urinary tract infections and chronic kidney disease in pets, especially cats. Zambori et al. (Scientific Papers: Animal Science and Biotechnologies, 2012, 45(2)) report that the importance of biofilm in disease processes in humans and animals is now widely recognized.

SUMMARY

This invention discloses a composition and method of use comprising the combination of several green and naturally derived ingredients and suitable carriers in a form suitable for use as biofilm penetrating and inhibiting composition and a wound healing composition for treating wounds containing biofilm and the methods of use thereof.

Based on the experimental data in the instant invention, combinations of LAE ($N^\alpha$ C8-C16 alkanoyl-L di-basic amino acid —$C_1$-$C_4$ alkyl ester being $N^\alpha$-lauroyl-L-arginine-ethyl ester)-HCl, SL (sucrose laurate), and ML (glycerol monolaurate) penetrate established *P. aeruginosa* biofilm and kill sessile (anchored) and planktonic (free floating) bacteria.

The instant invention discloses the use of a composition to inhibit biofilm formation and kill planktonic bacteria or fungi as well as biofilm bacteria or fungi on medical devices as well as contact lens, food preparation surfaces and the like.

It is the objective of this invention to present a novel and unanticipated approach using green and naturally derived food ingredients that can effectively penetrate and reach bacteria imbedded in biofilm that may be found in a wound, in surgical devices, in body cavities such as nasal passages, vaginal areas, or on animal and human food processing equipment.

Another objective of this invention is to present a system to penetrate and reach the bacteria in mature biofilm cells and kill it, while also killing the planktonic cells that form the biofilm.

A third object of this invention is to provide means treat wounds with a system that does not require daily changes. A fourth object of this invention is to provide a safe and non-cytotoxic system for biofilm penetration and inhibition. A fifth object of this invention is to reduce biofilm and inhibit the growth or reconstitution of additional biofilm.

Biofilm containing bacteria can occur in or on the body, e.g. in wounds, burns, in oral care whereby plaque is considered biofilm, in the nasal cavity, in skin acne, in the ear, in contact lens, etc. The compositions can be used as storage solutions or a disinfecting system for contact lenses or to inhibit or kill planktonic and sessile cells because contact lenses frequently have biofilm. Biofilms can be found in or on medical or dental devices or equipment, or surgical instruments used for procedures where it is difficult to reach/penetrate biofilm, e.g. in surgical instruments such as endoscopes, etc. These compositions are used as a coating on existing medical devices or dental devices, e.g. surgical implants and similar devices, medical/dental/surgical equipment, etc. to inhibit the formation of biofilms.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments in which the principles of the invention are utilized, and the accompanying drawings of which:

FIG. 6A-B depicts the formulas tested and results after treatment with the compositions of the present invention according to Example 6.

FIG. 7 depicts the formulas tested and results after treatment with the compositions of the present invention according to Example 7.

FIG. 8A-B depicts the formulas tested and results after treatment with the compositions of the present invention according to Example 8.

DETAILED DESCRIPTION

Figures 1A, 1B:
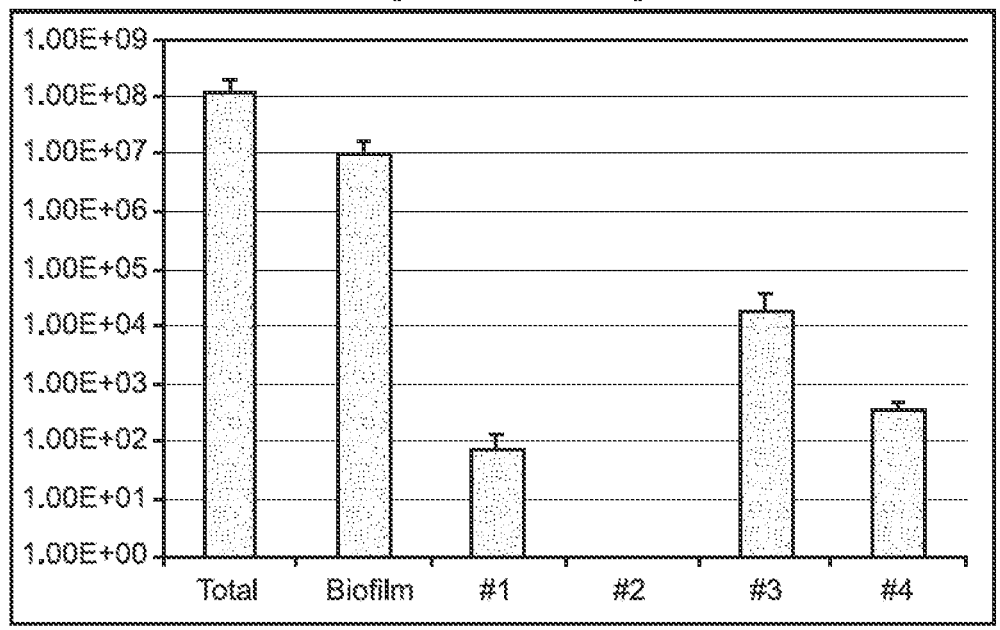
FIG. 1A-B depicts the formulas tested and results after treatment with the compositions of the present invention according to Example 1.

One embodiment of the invention is a method of killing or inhibiting planktonic bacteria or fungi and bacteria or fungi embedded in a biofilm comprised of at least a matrix and bacteria, the method comprising: applying to a surface of the biofilm a composition having an active ingredient comprising at least two or more of: a) a salt having a cation $N^\alpha$ C8-C16 alkanoyl-L di-basic amino acid —C1-C4 alkyl ester and an anion selected from the group consisting of: halide, nitrite, nitrate, linolenate, laurate, oleoate, phenolate, polyphenolate, carboxylate, hydroxycarboxylate, hyaluronate, antibiotic anion, resveratrol, and an amino acid, the salt being present in an amount from about 0.025 wt % to about 10 wt %; b) a glycerol monoester of a fatty acid being present in an amount from about 0.05 wt % to about 20 wt %; and c) a sugar ester of a fatty acid being present in an amount from about 0.075 wt % to about 30 wt %. To this active ingredient composition can optionally be added one or more of: d) a solvent being present in an amount from about 20 wt % to about 99.9 wt %; or e) a thickener or carrier or gelling agent being present in an amount from about 20 wt % to about 75 wt %; or f) a sacrificial agent being present in an amount from about 0.05 wt % to about 5 wt %; or g) a hydrogel having a three-dimensional hydrophilic polymer network. In this method, the active ingredient of the composition killing or inhibiting planktonic bacteria or fungi and penetrating the biofilm matrix and killing or inhibiting biofilm bacteria or fungi.

Even more specifically, the method may be characterized by: the a) Na C8-C16 alkanoyl-L di-basic amino acid —C1-C4 alkyl ester being $N^\alpha$-lauroyl-L-arginine-ethyl ester; or the b) glycerol monoester a fatty acid being monolaurin; or the c) sugar ester of a fatty acid being sucrose laurate; or the d) solvent being at least one of: water, 1,2-propylene glycol or 1,3-propylene glycol, 1,2-pentanediol, sorbitol, glycerol, xylitol, polyethylene glycol, polypropylene glycol, butylene glycol, pentylene glycol, hexylene glycol; or the e) thickener or carrier or gelling agent being at least one of: a polymer, a hydrocolloid, an acrylate, an acrylamide, a carboxylated cellulose, lecithin, poly(lactic-co-glycolic acid) (PLGA), polymeric ethers, polymeric aliphatic alcohols, polyalkoxylated alcohols, naturally occurring high molecular weight substances such as sodium alginate, gums, xanthan gum, gum tragacanth, starch, collagen aluminum silicate, quince seed extract, semi-synthetic high molecular substances such as methyl cellulose, carboxymethyl cellulose, hydroxyethylcellulose, hydroxypropylcellulose, hydroxypropylmethyl cellulose (HPMC), soluble starch and cationized cellulose, synthetic high molecular substances such as carboxyvinyl polymer and polyvinyl alcohol, arabic gum, carbomer, polyethylene oxide, poloxamer; or the f) sacrificial agent being at least one of: triethyl citrate, trimethyl citrate, or zinc glycinate; or the g) hydrogel being at least one of: polyvinyl alcohol, polyvinylpyrrolidone, polyethyleneimine, polyacrylic acid, polyhydroxyethyl-methacrylate, polyvinyl alcohol-glycine co-polymer, or polyvinyl alcohol-lysine co-polymer.

The compositions and methods in at least one embodiment of the invention treat biofilm covering a wound, or in medical tubing, or on medical instruments, or in devices, or in wound drainage tubes, or in human or on animal food processing or packaging equipment, or on food conveyor belts, or on pet chew toys, or in animal water bowls, or on floating toys, or in piping or in or on contact lens.

In yet another embodiment, methods of delivering an antibiotic, an antimicrobial, or a benefit agent to planktonic bacteria or fungi or biofilm bacteria or fungi are provided. Specifically, a composition is formed by adding to the composition comprising at least two of a), b) or c) and optionally d)-g) the ingredient h) a benefit agent comprising an antibiotic, an antimicrobial, or a drug. The benefit agent may be solubilized in a hydrogel and then added to the remaining ingredients of the composition. When this novel composition is applied to a biofilm, the composition of a) through f) acts as a delivery means for the benefit agent of h) to both planktonic bacteria or fungi and to biofilm bacteria or fungi by penetrating the biofilm matrix to deliver the benefit agent.

In yet another embodiment, a method of preserving a surface or product by preventing or inhibiting biofilm formation by bacteria or fungi is provided that comprises applying to a surface or adding to a product a composition having an active ingredient comprising at least two or more of: a) a salt having a cation $N^\alpha$ C8-C16 alkanoyl-L di-basic amino acid —C1-C4 alkyl ester and an anion selected from the group consisting of: halide, nitrite, nitrate, linolenate, laurate, oleoate, phenolate, polyphenolate, carboxylate, hydroxycarboxylate, hyaluronate, antibiotic anion, resveratrol, and an amino acid, the salt being present in an amount from about 0.025 wt % to about 10 wt %; b) a glycerol monoester of a fatty acid being present in an amount from about 0.05 wt % to about 10 wt %; and c) a sugar ester of a fatty acid being present in an amount from about 0.075 wt % to about 20 wt %. To the active ingredients of the composition a d) a solvent being present in an amount from about 20 wt % to about 99.9 wt %; or e) a thickener or carrier or gelling agent being present in an amount from about 20 wt % to about 75 wt %; or f) a sacrificial agent being present in an amount from about 0.05 wt % to about 5 wt %; or g) a hydrogel having a three-dimensional hydrophilic polymer network may be added. In this method, the active ingredient of the composition acting as a preservative by preventing or inhibiting bacteria or fungi from forming a biofilm on a surface or in a product.

The methods may also be characterized by the a) $N^\alpha$ C8-C16 alkanoyl-L di-basic amino acid —C1-C4 alkyl ester being $N^\alpha$-lauroyl-L-arginine-ethyl ester; or the b) glycerol monoester a fatty acid being monolaurin; or the c) sugar ester of a fatty acid being sucrose laurate; or the d) solvent being at least one of: water, ethanol, 1,2-propylene glycol or 1,3-propylene glycol, 1,2-pentanediol, sorbitol, glycerol, xylitol, polyethylene glycol, polypropylene glycol, butylene glycol, pentylene glycol, hexylene glycol; or the e) thickener or carrier or gelling agent being at least one of: a polymer, a hydrocolloid, an acrylate, an acrylamide, a carboxylated cellulose, lecithin, poly(lactic-co-glycolic acid) (PLGA), polymeric ethers, polymeric aliphatic alcohols, polyalkoxylated alcohols, naturally occurring high molecular weight substances such as sodium alginate, gums, xanthan gum, gum tragacanth, starch, collagen aluminum silicate, quince seed extract, semi-synthetic high molecular substances such as methyl cellulose, carboxymethyl cellulose, hydroxyethylcellulose, hydroxypropylcellulose, hydroxypropylmethyl cellulose (HPMC), soluble starch and cationized cellulose, synthetic high molecular substances such as carboxyvinyl polymer and polyvinyl alcohol, arabic gum, carbomer, polyethylene oxide, poloxamer; or the f) sacrificial agent being at least one of: triethyl citrate, trimethyl citrate, or zinc glycinate; or the g) hydrogel being at least one of: polyvinyl alcohol, polyvinylpyrrolidone, polyethyleneimine, polyacrylic acid, polyhydroxyethyl-methacrylate, polyvinyl alcohol-glycine co-polymer, or polyvinyl alcohol-lysine co-polymer.

The methods may be applied to a surface being selected from the group consisting of: microcapsules, wound dressings, implants, wound closures, staples, meshes, controlled drug delivery systems, wound coverings, fillers, sutures, tissue adhesives, tissue sealants, absorbable and non-absorbable hemostats, catheters, wound drainage tubes, arterial grafts, soft tissue patches, gloves, shunts, stents, guide wires and prosthetic devices, contact lens, medical devices, food processing equipment, food conveyor belts, food packaging equipment, pet or animal food, pet chew toys, pet or animal water bowls, cosmetics, and floating toys.

The methods may be used for preserving the products selected from the group consisting of: cosmetics and personal care items.

Compositions for penetrating a biofilm matrix and killing both planktonic and biofilm bacteria or fungi that have an active ingredient comprising at least two or more of: a) a salt having a cation $N^\alpha$ C8-C16 alkanoyl-L di-basic amino acid —C1-C4 alkyl ester and an anion selected from the group consisting of: halide, nitrite, nitrate, linolenate, laurate, oleoate, phenolate, polyphenolate, carboxylate, hydroxycarboxylate, hyaluronate, antibiotic anion, resveratrol, and an amino acid, the salt being present in an amount from about 0.025 wt % to about 10 wt %; b) a glycerol monoester of a fatty acid being present in an amount from about 0.05 wt % to about 10 wt %; and c) a sugar ester of a fatty acid being present in an amount from about 0.075 wt % to about 20 wt %; and optionally comprising one or more of: d) a solvent being present in an amount from about 20 wt % to about 99.9 wt %; or e) a thickener or carrier or gelling agent being present in an amount from about 20 wt % to about 75 wt %; or f) a sacrificial agent being present in an amount from about 0.05 wt % to about 5 wt % are provided; or g) a hydrogel having a three-dimensional hydrophilic polymer network.

The composition may be further characterized by: the a) $N^\alpha$ C8-C16 alkanoyl-L di-basic amino acid —$C_1$-$C_4$ alkyl ester being $N^\alpha$-lauroyl-L-arginine-ethyl ester; or the b) glycerol monoester a fatty acid being monolaurin; or the c) sugar ester of a fatty acid being sucrose laurate; or the d) solvent being at least one of: water, 1,2-propylene glycol or 1,3-propylene glycol, 1,2-pentanediol, sorbitol, glycerol, xylitol, polyethylene glycol, polypropylene glycol, butylene glycol, pentylene glycol, hexylene glycol; or the e) thickener or carrier or gelling agent being at least one of: a polymer, a hydrocolloid, an acrylate, an acrylamide, a carboxylated cellulose, lecithin, poly(lactic-co-glycolic acid) (PLGA), polymeric ethers, polymeric aliphatic alcohols, polyalkoxylated alcohols, naturally occurring high molecular weight substances such as sodium alginate, gums, xanthan gum, gum tragacanth, starch, collagen aluminum silicate, quince seed extract, semi-synthetic high molecular substances such as methyl cellulose, carboxymethyl cellulose, hydroxyethylcellulose, hydroxypropylcellulose, hydroxypropylmethyl cellulose (HPMC), soluble starch and cationized cellulose, synthetic high molecular substances such as carboxyvinyl polymer and polyvinyl alcohol, arabic gum, carbomer, polyethylene oxide, poloxamer; or the f) sacrificial agent being at least one of: triethyl citrate, trimethyl citrate, or zinc glycinate; or the g) hydrogel being at least one of: polyvinyl alcohol, polyvinylpyrrolidone, polyethyleneimine, polyacrylic acid, polyhydroxyethyl-methacrylate, polyvinyl alcohol-glycine co-polymer, or polyvinyl alcohol-lysine co-polymer.

In yet another embodiment a device or product treated with the composition is provided. The device may be made by a process comprising impregnating, dipping, coating or soaking the device with the composition. The device being selected from the group consisting of: microcapsules, wound dressings, surgical implants, wound closures, staples, meshes, controlled drug delivery systems, wound coverings, medical fillers, sutures, tissue adhesives, tissue sealants, absorbable and non-absorbable hemostats, catheters, wound drainage tubes, arterial grafts, soft tissue patches, gloves, shunts, stents, surgical guide wires, prosthetic devices, contact lens, endoscopes, dentures, medical devices, food processing equipment, food conveyor belts, food packaging equipment, pet or animal food, pet chew toys, pet or animal water bowls, and floating toys. The product made by a process of mixing the composition with the product.

In yet another embodiment, a wound covering for chronic wounds that does not adhere to the wound surface, is held stable at the wound site, and has water absorbing properties, the wound covering further comprising: an outer protective covering that does not contact the surface of the chronic wound; means for securing dressing to a wound site; and a surface that is in contact with the chronic wound comprising synthetic polymers, natural polymers or a combination thereof that absorb water and release the composition to the surface of the chronic wound.

In yet another embodiment the composition may further comprise h) at least one bioactive agent. The bioactive agent may be substantially water-insoluble antimicrobial or drug. The bioactive material may be solubilized by the g) hydrogel.

Some embodiments refer to planktonic and biofilm bacteria or fungi. Planktonic bacteria or fungi are understood to be bacteria or fungi that are free floating or are otherwise unattached to a matrix. These bacteria may be located on the surface of a biofilm matrix or between a biofilm matrix and a surface, such as a wound bed or a device. These planktonic bacteria or fungi are phenotypically distinguishable from bacterial that are located in the biofilm matrix. The term biofilm bacteria or fungi, or sessile bacteria or fungi or embedded bacteria or fungi refer generally to bacteria or fungi that are either physically attached to a surface or a biofilm matrix or trapped therein.

The compositions and methods described herein are useful for killing or inhibiting both planktonic and biofilm bacteria or fungi. It is not necessary to kill bacteria or fungi for the compositions to be effective, merely that the bacteria or fungi are inhibited from form a biofilm or forming an attachment to a surface or in a product so as to enable biofilm formation to begin.

The compositions described must have at least two active ingredients. However, all three active ingredients may also be used in combination and at any concentration.

The compositions described are useful for prevention and treatment of biofilm on an unlimited number of surfaces. Practically, any surface upon which a biofilm may form is encompassed by the present invention. This is particularly the case because of the beneficial features of the compositions, namely being nontoxic, generally recognized as safe, and consumable, they may be used on any surface.

The compositions described are also useful as preservatives when mixed with personal care items or cosmetics as preventing biofilm formation.

With respect to hydrogels, a hydrogel is a network of polymer chains that are hydrophilic, absorbent, flexible and are made of natural or synthetic polymeric networks. The hydrogel is not limited to a specific shape or form. A hydrocolloid is a substance that forms a gel in the presence of water.

While various embodiments described herein refer to killing or inhibiting bacteria or preventing bacteria from forming a biofilm, it is fully appreciated that the inventive methods and compositions also encompass killing or inhibiting yeasts, fungi, molds, and any type of bacteria or other microorganism that can adhered or otherwise become attached to a surface and form a microorganism/matrix complex likened to biofilm. A biofilm may contain a mixture of different types of microorganisms, such as yeast and mold and bacteria.

Various embodiments herein may recite the term "including" or in the claims the term "comprising", and their grammatical variants. For each such embodiments, corresponding additional embodiments are explicitly contemplated where the term "comprising" is replaced with "consisting essentially of" and "consisting of". For example, a composition comprising a) a salt having a cation $N^\alpha$ C8-C16 alkanoyl-L di-basic amino acid —C1-C4 alkyl ester, b) a glycerol monoester of a fatty acid, c) a sugar ester of a fatty acid, d) a solvent, e) a thickener, a sacrificial agent. May consist essentially of the listed ingredients a)-f) or may consist of only the listed ingredients a)-f). Similar terminology would also apply to compositions further comprising g) a hydrogel and h) a benefit agent.

The term "wt %" is equivalent to wt %, or wt. %, or wt. %, or % of the final formulation. The term wt % represents the amount of an ingredient in comparison with the weight of the total formulation. As the chemical structure of some compounds is known, and therefore the molecular weight of specific compounds is known, the mol % may also be calculated if desired.

It must be noted that to kill bacteria in biofilm, the biofilm must be penetrated. In order to kill bacteria in biofilm, the biofilm exopolysaccharide matrix needs to be penetrated in order to reach the bacteria. In the Examples of the instant invention the complete kill of the planktonic and biofilm bacteria (also referred to as "bioburden") is shown by compositions of the instant invention.

It is well known that *Pseudomonas aeruginosa* can produce biofilm on wounds, which is difficult to treat effectively. The ex vivo model used for data generation in the instant invention was reported by Phillips et al. (International Wound Journal, ISSN 1742-4801, J. Wiley and Sons, 2013).

Two GRAS approved food additives were experimentally found to be unexpectedly active in the presence of LAE-HCl as penetrating biofilm whereby it has been shown to reduce *Pseudomonas aeruginosa* in both planktonic and sessile cells by up to a ten log reduction as reported in the examples. These two GRAS approved food additive are monolaurin (also referred in this disclosure as "glycerol monolaurate" or "GML" or "ML") and sucrose mono-fatty esters (C8-C18), e.g. sucrose laurate (referred to in this disclosure as "SL"), sucrose myristate, sucrose palmitate, or sucrose stearate. Also unexpectedly the data in the examples show that a combination of at least two of the three ingredients in the instant invention, i.e. LAE, ML, and SL, will produce clinically significant biofilm penetration and kill in the Phillips et al. ex vivo model. The compositions described herein are capable of diminishing or eliminating biofilm formation by complete kill with no regrowth of the microorganism.

The amount of $N^\alpha$ C8-C16 alkanoyl-L di-basic amino acid —C1-C4 alkyl ester salts, can range from about 0.025 wt % to about 10.0 wt. % based on the total weight of the final formulation. The preferred amount of $N^\alpha$ C8-C16 alkanoyl-L di-basic amino acid —C1-C4 alkyl ester salts may also range from about 0.05 wt % to about 10.0 wt % or between about 0.1 wt % to about 10.0 wt %; or between about 0.2 wt % to about 10.0 wt %; or between about 5 wt % to about 10.0 wt %; or between about 0.05 wt % to about 5 wt %; or between about 0.05 wt % to about 1 wt %. The preferred amount of $N^\alpha$ C8-C16 alkanoyl-L di-basic amino acid —C1-C4 alkyl ester salts may also include any single wt % encompassed by the range of between about 0.05 wt % to about 10.0 wt %, including for example, 0.05 wt %, 0.1 wt %, 1 wt. % or the like. The preferred amount of LAE salts can range from about 0.05 wt % to about 5.0 wt % based on the total weight of the final formulation. The invention encompasses any individual amount encompassed by this range, including but not limited to for example about 5.0 wt %, about 1.0 wt % etc., the weight percent being based on the total weight of the final formulation.

The amount of glycerol monoester of a C8-C14 fatty acid, such as for example monolaurin (ML) can range from about 0.05 wt % up to about 20.0 wt. % based on the total weight of the final formulation. The preferred amount of a glycerol monoester of a C8-C14 fatty acid may also range from about 0.1 wt % to about 20.0 wt % or between about 1 wt % to about 20.0 wt %; or between about 0.05 wt % to about 18.0 wt %; or between about 0.05 wt % to about 10.0 wt %; or between about 0.05 wt % to about 5 wt %. The preferred amount of glycerol monoester of a C8-C14 fatty acid may also include any single wt % encompassed by the range of between about 0.05 wt % to about 20.0 wt %, including for example, 0.05 wt %, 1 wt. %, 10 wt %, or the like. The invention encompasses any individual amount encompassed by this range, including but not limited to for example about 2.0 wt %, about 1.0 wt % etc., the weight percent being based on the total weight of the final formation.

The range of the sucrose C8-C18 fatty acid monoesters can range from about 0.075 wt % to about 30.0 wt % based on the total formulation. The preferred amount may also of the sucrose C8-C18 fatty acid monoesters may also range from about 0.075 wt % to about 10.0 wt % based on the total formulation, or between about 0.075 wt % to about 10.0 wt %; or between about 0.075 wt % to about 5.0 wt %, or between about 3 wt % to about 30.0 wt %, or about 10 wt % to about 30.0 wt % The invention encompasses any individual amount encompassed by this range, including but not limited to for example about 10.0 wt % or about 1.0 wt % etc., the weight percent being based on the total weight of the final formation.

Major Ingredients

A combination of two GRAS approved food additives were experimentally found to be active as penetrating biofilm whereby it has been shown to reduce *Pseudomonas aeruginosa* in both planktonic and sessile cells.

LAE-HCl $N^\alpha$-long chain alkyl di-basic amino acid alkyl ester acid salts have been known since the 1960'. One of the first patents to recommend these amino acids, specifically for food applications was U.S. Pat. No. 3,825,560. A number of derivatives are disclosed include $N^\alpha$-cocoyl-L-arginine ethyl ester pyrolidone carboxylate and $N^\alpha$-lauroyl-L-arginine methyl ester hydrochloride.

Extensive toxicological and metabolic experiments are reported for $N^\alpha$-lauroyl L-arginine ethyl ester monohydrochloride (LAE-HCl)(Food and Chemical Toxicology, 42 (2004), p 242-259).

US Pub. Appln. No. 2011/10230558 discloses LAE compounds are known to destroy endotoxins produced by some bacteria. Another advantage of the instant invention is that L-arginine derivatives of LAE has a positive charge and will react with anionic hydrocolloids that are used for wound healing dressings.

Biofilm Inhibition by LAE

Musk et al. (Chemistry & Biology, Vol. 12, 789-796, July, 2005) write that bacterial biofilms are thought to aid in the survivability of a variety of intractable infections in humans. Ferric ammonium citrate inhibited biofilm formation in a dose-dependent manner. *P. aeruginosa* strains taken from the sputum of 20 CF patients showed a similar response to elevated iron levels. Cai et al (Brazilian Journal of Microbiology, ISSN 1517-8382), indicate that *Pseudomonas aeruginosa* is one of the major causes of nosocomial infections. In addition, *P. aeruginosa* is a leading pathogen among patients with cystic fibrosis, diffuse panbronchiolitis, and chronic obstructive pulmonary disease. In patients with these underlying diseases, it can cause chronic infections characterized by the formation of biofilms. Therefore, infections with biofilm-forming bacteria are persistent and difficult to treat with antibiotics. Iron is essential for most pathogens because iron is an indispensable component of many proteins, especially some enzymes in bacteria. Therefore, iron acquisition from environment is important for the growth and metabolism of *P. aeruginosa*. Recently, many studies revealed that iron also play an important role in biofilm formation. In vitro experiments showed both iron-depletion (<1 μM) and iron-repletion (>100 μM) retarded biofilm formation. Furthermore, some reports showed that the level of free iron is increased in airway secretions of cystic fibrosis patients, and this might be one of the possible reasons for the frequent identification of biofilms in the lungs of these patients. According to Braun et al. (Springer Briefs in Biometals, DOI: 10.1007/978-94-007-6088-2_2), iron is an essential element for many key redox systems. It is difficult to acquire for cells under oxic conditions, since $Fe^{3+}$ forms insoluble hydroxides.

Kim et al. (Frontiers in Microbiology, Vol. 8, May 2017) report that *Pseudomonas aeruginosa* is a ubiquitous gram-negative bacterium capable of forming a biofilm on living and non-living surfaces, which frequently leads to undesirable consequences. They found that lauroyl arginate ethyl (LAE), a synthetic non-oxidizing biocide, inhibited biofilm formation by *P. aeruginosa* at a sub-growth inhibitory concentration under both static and flow conditions. Thus LAE generated iron-limiting conditions, and in turn, blocked iron signals necessary for *Pseudomonas aeruginosa* biofilm development. As destroying or blocking signals leading to biofilm development would be an efficient way to mitigate problematic biofilms, these findings suggest that LAE can aid in reducing *Pseudomonas aeruginosa* biofilms for therapeutic and industrial purposes. LAE activated the genes involved in iron acquisition (e.g., the pyoverdine and pyochelin related genes) and increased twitching motility, due to the low availability of iron to *P. aeruginosa* because LAE chelated the iron.

It was found in the experimental results that an effective amount of antimicrobial agent like LAEHCl was between about 0.05 to about 5.0 wt % based on the total amount of the formula. If the LAE salt has an anion other than a halide, e.g. C8-C23 carboxylate or polyphenolate anion, then the amount is proportional to the molecular weight of the anion.

While this instant invention discloses the antimicrobial LAE salts, both in water-soluble, and lesser water-soluble form having a controlled release property as disclosed by allowed patents as listed previously, other antimicrobials can be used such as chlorhexidine salts, cetylpyridinium halide, monomeric or polymeric quats, PHMB salts, diallyl dimethyl ammonium halide (Merquat™), defensins, cationic antibiotics, monovalent silver, or combinations thereof may be used in the disclosed methods of biofilm penetrating to deliver other antimicrobials, antibiotics, and silver and nano-silver.

The preferred di-basic amino acid derivative in this invention is $N^\alpha$ lauroyl-L-arginine ethyl ester. Some preferred salts of LAE are the HCl, linolenate, laurate, oleoate, nitrate, nitrite salts and various salts containing antioxidants having a phenolate or polyphenolate anion and/or carboxylate functionalities. Another lesser preferred compound is the L-lysine corresponding compound. LAE has excellent antimicrobial activity of a broad nature including gram positive, gram negative, molds, yeast and other type microorganisms, and it is also effective against endotoxins. Other desirable properties of LAE are non-toxic, biodegradable and its metabolic breakdown to form arginine, lauric acid and ethanol, which all of these compounds are found in the human body as natural materials and present no toxicological problems.

LAE metabolizes to arginine which is a semi essential amino acid. Arginine is non-essential because the body can produce it, however, under period of growth, illness and metabolic stress not enough arginine is produced by the body. Arginine regulates many metabolic and physiologic body functions and has several attributes that support wound repair like the following: has 32% nitrogen; is a precursor to proline, which is converted to hydroxyproline, then to collagen; has a positive influence on the body's levels of insulin like growth factor (IGF-I), a hormone that promotes wound healing; is the only amino acid substrate for nitric oxide synthesis (Nitric oxide has a beneficial effect on circulatory status and increases blood supply to the wound); contains immune enhancing properties that reduce the risk of wound complications; will break down to form NO, a desirable compound which stimulates the healing process.

Solubilizing and Surfactants

Solubilizing the biofilm matrix is very important because it is been proven that dead cells are inflammatory (U.S. Pub. App. No 2010/0183519). The use of a poloxamer, e.g. poloxamer-188 or poloxamer-407, as thickening agents or carriers or gelling agents for the instant invention can be used. Any suitable and/or acceptable gelling or thickening or carrier agents can be used in the instant invention including polymers like hydrocolloids, acrylates, acrylamides, carboxylated celluloses.

U.S. Pat. No. 9,283,278 describe a method for treating a microbial biofilm on a patient including the steps of contacting the microbial biofilm with a composition comprising a surface active agent and a sub-lethal amount of an antimicrobial agent. The surface active agent of embodiments may be a poloxamer, meroxapol, poloxamine or combinations thereof.

Surfactants disrupt biofilm structural integrity by causing structural disturbance of proteinaceous matrix components. Surfactants might also disrupt the cell membrane and thereby weaken or release extracellular polymeric substance (EPS) molecules that are putatively anchored to the cell via a membrane interaction (U.S. Pat. No. 9,283,278 and Montana State University thesis by Xiao Chen "Chemically Induced Biofilm Detachment" (1998)).

Lecithin

It has been found that lecithin can aid in penetrating biofilms. Lecithins are mixtures of glycerophospholipids including phosphatidylcholine, phosphatidylethanolamine, phosphatidylinositol, and phosphatidic acid. Lecithin has emulsification and lubricant properties, and is a surfactant. It can be totally metabolized by humans, so is well tolerated by humans and nontoxic when ingested; some other emulsifiers can only be excreted via the kidneys. The major components of commercial soybean-derived lecithin are: 33-35% soybean oil, 20-21% inositol phosphatides, 19-21% phosphatidylcholine, 8-20% phosphatidylethanolamine, 5-11% other phosphatides, 5% free carbohydrates, 2-5% sterols, and 1% moisture. Lecithin is used for applications in human food, animal feed, pharmaceuticals, paints, and other industrial applications.

Hydrophilic-Lipophilic Balance or "HLB" is an index of the predicted preference of an emulsifier for oil (O) or water (W)—the higher the HLB, the more hydrophilic the molecule; the lower the HLB, the more hydrophobic the molecule. Typical usage levels of lecithin in an emulsion system are: 1-5% of the fat for W/O; 5-10% of the fat for O/W. The amount of lecithin used is dependent upon factors such as the pH, the inclusion of proteins and, and the salt concentration.

Coating Implant with LAE-Hyaluronic Salt

In the instant invention an implant can be coated with LAE-hyaluronic acid salt as the LAE component of the instant invention. Also, the implant can be a metal, a metal alloy, a ceramic, or a combination thereof. Also a multi-coated implant comprising: (a) a first layer residing on the surface of the implant; and (b) a second layer comprising LAE-hyaluronic acid residing on the first layer.

The coated implant resists microbial growth. Examples of microbial growth that can be resisted include, but are not limited to *Staphylococcus aureus* and *Staphylococcus epidermidis*.

The coated implants of the invention can be bioabsorbable, resorbable, or permanent. The implants of the invention can be used in osteointegrative, osteosynthetic, orthopedic, and dental applications. Representative implants include, but are not limited to, void fillers (e.g., bone void fillers), adjuncts to bone fracture stabilization, intramedullary fixation devices, joint augmentation/replacement devices, bone fixation plates (e.g., craniofacial, maxillofacial, orthopedic, skeletal, and the like), screws, tacks, clips, staples, nails, pins, rods, anchors (e.g., for suture, bone, or the like), scaffolds, stents, meshes (e.g., rigid, expandable, woven, knitted, weaved, etc.), sponges, implants for cell encapsulation or tissue engineering, drug delivery devices (e.g., antivirals; antibiotics; carriers; bone ingrowth induction catalysts such as bone morphogenetic proteins, growth factors, peptides, and the like.), monofilament or multifilament structures, sheets, coatings, membranes (e.g., porous, microporous, and resorbable membranes), foams (e.g., open cell and closed cell foams), screw augmentation devices, cranial reconstruction devices, a heart valve, and pacer lead.

The term "hyaluronic acid," as used herein includes a (co)polymer of acetylglucosamine ($C_8H_{15}NO_6$) and glucuronic acid ($C_6H_{10}O_7$) occurring as alternating units.

Representative materials for the implant include, but are not limited to, metals and metal alloys (e.g., titanium, titanium alloy, nickel-titanium alloy, tantalum, platinum-iridium alloy, gold, magnesium, stainless steel, chromo-cobalt alloy); ceramics; and biocompatible plastics or polymers (e.g., polyurethanes and/or poly(α-hydroxy ester)s such as polylactides, polyglycolides, polycaprolactones, and the like, and combinations and/or copolymers thereof). Other non-limiting examples of implants include those made from materials disclosed in any of the following U.S. Pat. Nos. 4,503,157; 4,880,610; 5,047,031; 5,053,212; 5,129,905; 5,164,187; 5,178,845; 5,279,831; 5,336,264; 5,496,399; 5,569,442; 5,571,493; 5,580,623; 5,683,496; 5,683,667; 5,697,981; 5,709,742; 5,782,971; 5,820,632; 5,846,312; 5,885,540; 5,900,254; 5,952,010; 5,962,028; 5,964,932; 5,968,253; 6,002,065; 6,005,162; 6,053,970; 6,334,891. The implant can be substantially free of a polymeric component (i.e., a plastic or polymer).

Non-limiting examples useful implants substantially free of plastic or polymer include a bone void filler, an adjunct to bone fracture stabilization, an intramedullary fixation device, a joint augmentation/replacement device, a bone fixation plate, a screw, a tack, a clip, a staple, a nail, a pin, a rod, an anchor, a scaffold, a stent, a mesh, a sponge, an implant for cell encapsulation, an implant for tissue engineering, a drug delivery device, a bone ingrowth induction catalyst, a monofilament, a multifilament structure, a sheet, a coating, a membrane, a foam, a screw augmentation device, a cranial reconstruction device, a heart valve, or a pacer lead.

The LAE-hyaluronic acid salt provides an in vivo resistance to absorption, adhesion, and/or proliferation of a bacteria, such as *Staphylococcus aureus* or *Staphylococcus epidermidis*. Any method capable of forming a coating of the LAE-hyaluronic acid salt can be utilized to make the coated implants of the instant invention including, but not limited to dip-coating, application by a brush, spray coating, and any combination thereof. Examples of coating methods can be found in, e.g., U.S. Pat. Nos. 4,500,676, 6,187,369 and 6,106,889 and U.S. Pub. App. Nos. 2002/0068093 and 2003/0096131. Typically, a composition comprising the LAE-hyaluronic acid salt and an organic solvent is applied to the implant, and the resultant coated implant is allowed to dry or cure.

In the instant invention a multi-coated implant comprising: (a) a first coat residing on the surface of the implant; and (b) a second coat comprising the LAE-hyaluronic acid salt residing on the first coat is disclosed. Non-limiting examples useful first coats include metals (e.g., titanium, gold, or platinum), ceramic materials (e.g., hydroxyapatite or tricalcium phosphate, or polymers (e.g., an acrylic polymer base coat), or any combination thereof.

The first coat can be the same as, or different from, the implant material. Non-limiting examples of useful implant materials include metals, metal alloys, or ceramics as described above; and/or plastics or polymers, e.g., polyurethanes and/or poly(α-hydroxy ester) such as polylactides, polyglycolides, polycaprolactones, and the like; or any combination thereof.

Methods for coating the implant with a ceramic or polymer include those describe above for coating the implant with the LAE-hyaluronic acid salt. In certain embodiments, the LAE-hyaluronic acid salt coating can comprise one or more polymer additives. Without being limited by theory, the addition of a polymer, e.g., an elastic film forming polymer, can improve the structural characteristics of the LAE-hyaluronic acid salt coating such as can impart improved flexibility, adhesion and/or as resistance to cracking. Any polymer can be used provided the polymer is biocompatible and does not significantly interfere with the desired characteristics of the hyaluronic acid component. Typically, the polymer, when used, is bioadsorbable or erodible. More preferably, the polymer, when used, is bioadsorbable. A non-limiting examples of a useful polymers include polyurethane (see U.S. Pat. No. 4,500,676, the entire disclosure of which is incorporated herein as reference); polylactides; polyglycolides; homopolymers or copolymers of monomers selected from the group consisting of L-lactide; L-lactic acid; D-lactide; D-lactic acid; D,L-lactide; glycolide; α-hydroxybutyric acid; α-hydroxyvaleric acid; α-hydroxyacetic acid; α-hydroxycaproic acid; α-hydroxyheptanoic acid; α-hydroxydecanoic acid; α-hydroxymyristic acid; α-hydroxyoctanoic acid; α-hydroxystearic acid; hydroxybutyrate; hydroxyvalerate; β-propiolactide; β-propiolactic acid; γ-caprolactone; β-caprolactone; γ-butyrolactone; pivalolactone; tetramethylglycolide; tetramethylglycolic acid; dimethylglycolic acid; trimethylene carbonate; dioxanone; those monomers that form liquid crystal (co) polymers; those monomers that form cellulose; those monomers that form cellulose acetate; those monomers that form carboxymethylcellulose; those monomers that form hydroxypropylmethyl-cellulose (HPMC); polyurethane precursors comprising macrodiols selected from the group consisting of polycaprolactone, poly(ethylene oxide), poly (ethylene glycol), poly(ethylene adipate), poly(butylene oxide), and a mixture thereof, isocyanate-functional compounds selected from the group consisting of hexamethylene diisocyanate, isophorone diisocyanate, cyclohexane diisocyanate, hydrogenated methylene diphenylene diisocyanate, and a mixture thereof, and chain extenders selected from the group consisting of ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof; collagen, alginates (e.g., sodium or calcium alginate), polysaccharides such as chitin and chitosan, poly (propylene fumarate); and any mixture thereof. Similarly, the instant invention compositions that include $N^\alpha$ C8-C16 alkanoyl-L di-basic amino acid —C1-C4 alkyl ester salts, glycerol monoester of a C8-C14 fatty acid, and sucrose C8-C18 fatty acid monoesters can be incorporated into the biocompatible bioactive biomaterial for biofilm inhibition and penetration and bacteria kill. The instant invention discloses a combination of at least two out of the three ingredients, i.e. LAE/ML, LAE/SL, or ML/SL, as a coating onto surfaces, e.g., surgical implants, wires, catheters, etc., that can be solubilized in a non-aqueous solvent, e.g. ethanol, and then coated onto the surface to be inhibited. There will be hydrogen bonding between each ingredient and the surface to be coated as well as between each ingredients, thus developing bonds to improve adhesion to the surface and to each other.

Monolaurin and Sugar Esters of Fatty Acids

It has been shown in the examples that the combination of LAE salts with both sucrose monolaurate and monolaurin can kill both *Pseudomonas aeruginosa* planktonic cells as well as *Pseudomonas aeruginosa* biofilm bacteria cells. However it was unanticipated that, as shown in the experimental section of the disclosure, 1) sucrose monolaurate in combination with glycerol monolaurate w/o LAE salts can penetrate and result in clinically significant *Pseudomonas aeruginosa* planktonic and biofilm bacteria kill and also 2) sucrose monolaurate in combination with LAE salts w/o glycerol monolaurate can also penetrate and result in clinically significant *Pseudomonas aeruginosa* planktonic and biofilm bacteria kill.

Both glycerol monofatty esters and sugar monofatty esters have been reported as having preservative characteristics, primarily in foods but also in cosmetics ("Handbook of Preservatives")

Both monolaurin ("ML") and sucrose fatty esters have been reported to have some degree of biofilm inhibition and penetration properties (U.S. Pat. No. 5,284,833).

There are two factors to consider when choosing the glycerol monoester of a fatty acid. The ester part could be from C8-C14 saturated hydrocarbon, however the C12 has been consistently shown to be the optimal choice, since when esterifying glycerin it is possible to obtain di- and tri-esters as well as the monoester. Therefore in order to achieve the best antibacterial and biofilm dispersion, the monoester of monolaurin should be greater or equal to 70 wt % of the total ester content, the higher being the better. Preferred monoester level is 90 wt %.

Sugar Esters

In the United States, interest in the synthesis of sugar esters of fatty acids began in 1952, when the Sugar Research Foundation saw their surfactant potential. They are used as non-ionic surfactants, bleaching boosters and food additives.

Sucrose mono fatty esters according to the previous experiments are not active at 500 ppm or lower. Monolaurin is synergistic with LAE salts as while SL appears to enhance the antibacterial performance of LAE and of ML. For monolaurin this synergy is described in U.S. Pat. Nos. 8,193,244 and 9,023,891 and WO 2013/169231. For sucrose mono fatty esters the results are in the Examples.

Additional Ingredients

The instant invention discloses the use of certain chemicals to penetrate/disperse existing biofilm and/or prevent and/or inhibit biofilm formation and also that have antimicrobial activity. Additionally certain antimicrobials and antibiotics can be added to the wound healing and biofilm penetrating compositions of the instant invention. For $Na_2EDTA$, where a salt between the LAE based arginine derivative and the anions of ferulic acid, gallic acid, $Na_2EDTA$ can be formed in a 1:1 or 2:1 molar ratio, where the LAE based arginine derivative is either 1 or 2 molar equivalents to the $Na_2EDTA$. The $Na_2EDTA$ can also be used as a chelating agent and also as an additive with the arginine derivative.

Solvents

In some cases it may be necessary to include up to a maximum of about 40 wt % of a safe, green, and non-toxic solvent to the aqueous gel formulation to act as a solubilizer to dissolve all of the ingredients in the biofilm penetrating/wound healing composition. A partial list might include 1,2-propylene glycol or 1,3-propylene glycol, glycerol, polyethylene glycols, polypropylene glycols, butylene glycol, pentylene glycol, hexylene glycol or combinations thereof. Even though sorbitol or xylitol are solids, they form very concentrated aqueous solutions that can be used in this invention. In fact xylitol is a known anti-adhesive for bacteria binding to a variety of surfaces. A solubilizer such as propylene glycol or similar is necessary for monolaurin and LAE salts under certain conditions. However the level of the solubilizer is important as cytotoxicity is a concern with higher levels of solubilizer. For example, propylene glycol can be used to solubilize the LAE salts and monolaurin, and then this phase can be added to the water phase containing the sucrose laurate. Sucrose fatty esters can also used in the instant invention as solubilizers for monolaurin. Ethylene glycol is a known toxin, but propylene glycol has an acute oral toxicity of 20.0 g/kg ($LD_{50}$) as reported by R. J. Louis Sr ("Dangerous Properties of Industrial Materials", eighth addition, Van Nostrand, Reinhold, New York 1992).

Solvents can also reinforce the antimicrobial agents and help penetrate the active ingredients into the skin. So the selection of the proper solvent system can play an important role. For example in Acta. Derma. Venereal., 1991, 71 (2), pp 148-150, it was reported that 10 wt % of hexylene glycol was equivalent to 30 wt % of 1,3 butylene glycol or propylene glycol in vitro against *Streptococcus pyogenes, Streptococcus mitis, Staphylococcus epidermidis*, and *E. coli* in terms of killing power. 1,2-pentanediol is another solvent which has desirable properties such as excellent moisturizing, broad-spectrum antimicrobial activity, excellent as a solubilizer, as well as a dissolution ability.

Sacrificial Enzyme Inhibitors

In some wounds it may be necessary to include a sacrificial enzyme inhibitor to maintain or enhance the efficacy of the antimicrobials and biofilm disruptors.

Ohkawa (J. of Biochem., 1979 v. 86, C31, pages 643-656) found that all 11 strains of *Pseudomonas aeruginosa* had esterases on the cell envelope. The enzymes to have specificity for long chain esters with hydrophilic groups. Some antimicrobials like LAE salts, the glycerol monoesters of C8-C18 fatty acids, and the sucrose mono fatty esters C8-C16 can be hydrolyzed by esterases present on bacterial cells. In order to inhibit enzymatic hydrolysis and maintain efficacy, a natural or synthetic enzyme inhibitor can be added to the formulation. In addition to the other ingredients of the instant invention, it has been found experimentally that the addition of triethyl citrate ("TEC") can act as an inhibitor of esterases and can act to enhance and prolong the antibacterial activity of LAE-HCl, monolaurin and SL. Triethyl citrate ("TEC") will also enhance and prolong the antibacterial activity of other LAE salts.

Esterase inhibitors, e.g. triethyl citrate, trimethyl citrate, and zinc glycinate will prolong activity of LAE salts, sucrose fatty esters, and monolaurin. This invention prefers the use of a sacrificial enzyme inhibitor such as a triester ($C_1$-C4) citrate like triethyl citrate. The oral $LD_{50}$ in rats is 7.0 cc/kg, a low toxicity molecule. In general the usage range of triethyl citrate is from about 0.05 to about 5.0 wt % based on the total weight of the formulation. The water solubility of triethyl citrate at 25° C. is 6.5 g/100 g of solution.

Wound Dressings or Covering

An effective wound covering must have 1) a positive effect for promoting wound healing, 2) exhibit a sufficient water absorbing property, thus can absorb a wound exudates, 3) does not adhere to the wound surface and 4) can be held stable at the affected part. Wound dressings can be comprised of either synthetic or natural polymers, or combinations of the two. For serious wounds the medical profession usually use hydrophilic or cross-linked hydrogels having good oxygen permeable. Many different polymers can be used for example polyacrylate and salts thereof, polyvinylpyrrolidone (PVP) and copolymers, polyalkylenes, polymethyl vinyl ether-maleic anhydride or dicarboxylate and copolymers, polyacrylamide and copolymers, alginate, gum Arabic, tragacanth gum, carrageenans, xanthan gum or other natural gums.

It is understood that many other synthetic or natural polymers with these desirable properties can be substituted by one skilled in the art. The hydrogel layer in U.S. Pat. No. 8,604,073 comprises a three-dimensional network formed by a hydrophilic polymer by ionic or chemical cross-linking, cryogel formation, or by an interpenetrating polymeric network using polyfunctional water soluble polymers, such as polyvinyl alcohol, polyvinylpyrrolidone, polyethyleneimine, polyacrylic acid, polyhydroxyethylmethacrylate, polylactic acid, polylactide, polyglycolide, poly epsilon-caprolactone, copolymers and mixtures thereof, poly vinyl alcohol-glycine co-polymer, and polyvinyl alcohol-lysine co-polymer. Ionic or chemical crosslinking of the hydrophilic polymers can be accomplished in the polyfunctional polymers included in the antimicrobial coatings of the invention.

For example, a hydrogel layer coating a substrate material with the antimicrobial coating is applied, dried to a predetermined extent, and reacted with a suitable ionic or chemical crosslinking agent or agents known in the art.

For example U.S. Pat. No. 6,399,092 discloses an anhydrous, hydrophilic wound dressing containing a superabsorbent polymer and an antimicrobial agent. It's anhydrous nature allows it, when applied to a wound site, to absorb wound fluid and slowly release its water-soluble active microbial agent into the wound. The combination is an anhydrous, hydrophilic gel base carrier which may be a poloxamer, e.g. block copolymers of ethylene oxide and propylene oxide, etc. or polyethylene glycol with a superabsorbent polymer, which may be a starch polymer, a graft copolymer of starch polyacrylonitrile and non-starch homopolymers of polyacrylonitrile or a poly(2-propenamide-co-2-propenoic acid sodium salt), a homopolymer, or a cellulose base superabsorbent polymer. The importance of the initial composition being anhydrous is that such is essential and critical to the consistent release of the effective concentration of the soluble active of the formulation as it interfaces with an open wound. Such is less likely to occur if the formulation initially contains water.

Another aspect of the instant invention involves the salt formation by reacting the $N^\alpha$-alkanoyl-L basic amino acid ethyl ester water soluble salts of this invention with a variety of ingredients commonly found in wound dressings having functionalities like carboxylic groups. Examples of suitable anionic polymers are: Alginates, oxidized celluloses, chitosan water soluble salt derivatives, poly acrylic acid or polyacrylate acid copolymers which incorporate an acid comonomer like itaconic acid, carboxyethylcellulose, hyaluronic acid, or combinations thereof. It is understood that many other synthetic or natural polymers with these desirable properties can be substituted by one skilled in this art.

For wound dressings the amino acid derivatives of this invention can react with the carboxylate groups of the dressing under basic conditions (NaOH solution) to yield a salt, which will slowly release by contact with the extuate of the wound. Both bound and unbound biocidals will be beneficial to healing. For burn wounds a combination of $Ag^{+1}$ and the compositions of the instant invention can be employed. Other salt anions of the di basic amino acid derivatives disclosed can have anions which can also have wound healing properties.

The usefulness of lucuma nut oil material (LNO) (J. of Cosmetic Dermatology, Vol. 9 Is. 3 p. 185-195 September 2010) has been described. One or more of these fatty acids can be utilized as the anionic portion of the long chain alkyl di-basic amino acid alkyl ester acid salts disclosed in the instant invention are preferred if controlled release of the cation is desired as well as the benefit of the anionic component.

Some of the fatty carboxylates of the invention, for example linolenic acid, are very expensive. These fatty acids exist in nature and after refining can be utilized. For example soy bean oil, corn oil, canola oil, safflower oil, sunflower oil and others have multiple fatty acid mixtures. The importance of lauric, myristic, palmitic, stearic, oleic, linoleic and linolenic as counter ions to make a low water soluble salts to the long chain alkyl di-basic amino acid alkyl ester acid cations are preferred if controlled release of the cation is desired. The above mentioned fatty acids have these requirements suitable for the purposes of the anionic portion of the LAE salts disclosed in the instant invention. Other long chain carboxylates include omega 3, 6 and 9 acids. EPA (eicosapentaenoic acid) and DHA (docosapentaenoic acid), both omega-3 acids found in fish oil, are also preferred.

A particular useful group of anions for the cationic dibasic amino acid derivatives of the instant invention are both natural and synthetic dietary flavonoids and phenolic and polyphenolic compounds such as: flavonals, flaovones, flavanones, resveratrol, chalcones, anthocyanidins, anthocyanins, isoflavones, phenolic acids, hydroxycinammates, stilbenes, and rutin. As the counter ion of the antibacterial cations of this invention, the flavonoids as listed above will have excellent antioxidant properties, which are useful for wound healing. Once a wound (burn) occurs, concentrations of reactive oxygen species such as hydroxyl singlet oxygen, hydroperoxyl, superoxide anions radicals increase in damaged tissue producing a condition known as oxidative stress. Hydrogen peroxide behaves similarly. Thus the healing of chronic wounds can be assisted by the use of antioxidants which is a part of the $N^\alpha$-alkanoyl-L basic amino acid ethyl ester antimicrobial agents of this invention, as an anion of the salt. This invention also teaches that mixtures of the preferred di-basic amino acid derivatives and the conjugate acid form of the antioxidant can be effective. Previous literature examples of using antioxidant as wound healing compositions include U.S. Pat. Nos. 5,667,501, 5,612,321, and U. S. Pub. Appl. No. 2006/0159732.

Some illustrative examples of flavonoids but not an exclusive list are the following: kaernpferal, quercetin, epicotechin, hesperatin, cyanidin, genistein, gallic acid, ferulic acid, salicylic acid, trans or cis resveratrol, catechin, syringic acid, toxifolin, epigallocatechin, curcumin and myricetin. Many more flavonoids exist which can be utilized to form biocidal flavonoids salts taught in this invention can be found in a text book entitled, "Plant phenolics and Human Health, Biochemistry, Nutrition and Pharmacology".

Alpha keto propionic acid is another compound useful in wound healing. It is commonly known as pyruvic acid. As with other enhancers of this invention it can be employed as: 1) an anion of the di-basic amino acid derivatives of this invention, or 2) as an admixture.

Pyruvic acid supplies energy to living cells through the citric acid cycle (Krebs cycle) when oxygen is present (aerobic respiration) and alternatively ferments to produce lactic acid when oxygen is lacking.

The salts of this invention can be easily prepared by a simple metathesis reaction, e.g., a water soluble cationic biocide like $N^\alpha$-alkanoyl-L-di basic amino acid ethyl ester and a water soluble anion. These metathesis reactions can be performed in water or alcohol, however, absolute alcohol is required for the resulting NaCl to precipitate.

Coatings

The compositions of the instant invention can be adhered to a substrate, e.g. a surgical implant, endoscope, medical device, catheter, suture, food processing conveyor belt, a food carrying conduit, etc.

Thickeners, Gelling Agents, Carrier Agents

Any medical or food grade suitable and/or acceptable gelling or thickening or carrier agents can be used in the instant invention. Examples of thickening agents include smectite gelling agent is a synthetic magnesiosilicate that is free of any heavy metal contaminants; naturally occurring high molecular substances such as sodium alginate, various gums, xanthan gum, gum tragacanth, starch, collagen aluminum silicate, quince seed extract; semi-synthetic high molecular substances such as methyl cellulose, carboxymethyl cellulose, soluble starch and cationized cellulose; synthetic high molecular substances such as carboxyvinyl polymer and polyvinyl alcohol; polymers like hydrocolloids, acrylates, acrylamides, carboxylated celluloses, arabic gum, carbomer, polyethylene oxide, poloxamer and mixtures thereof; hydrogels; hydrophilic synthetic polymers, sugars, glycerol, propylene glycol (PG), derivatives thereof, and combinations.

The use of a poloxamer, e.g. poloxamer-188 or poloxamer-407, as thickening agents or carriers or gelling agents for the instant invention can be used. In an embodiment, the said biofilm penetrating compositions and wound healing compositions comprises a gelling or thickening agent in the range of 0.2 to 75.0 wt %, together with one or more pharmaceutically acceptable carriers/excipients. The thickener may preferably be contained in an amount of 0.5 to 50 wt % with respect to the total weight of the composition. The thickener may more preferably be contained in an amount of 1.0 to 10 wt % with respect to the total weight of the composition Examples of carrier liquids include Poly(lactic-co-glycolic acid) (PLGA), polymeric ethers, polymeric aliphatic alcohols, either together or alone, polyalkoxylated alcohols, dextrin or carboxymethyl dextrin cross linked to epichlorohydrin, propylene glycol, hexylene glycol, dipropylene glycol, tripropylene glycol, glycerin, ethanol, propylene glycol methyl ether, dipropylene glycol methyl ether, dipropylene glycol, tripropylene glycol, ethanol, n-propanol, n-butanol, t-butanol, 2-methoxyethanol, 2-ethoxyethanol, ethylene glycol, isopropanol, isbutanol, 1,4-butylene glycol, 2,3 butylene glycol, 2,4-dihydroxy-2-methylpentane, trimethylene glycol, 1,3-butanediol, 1,4,-butanediol, and combinations thereof. Specific examples of pharmaceutically acceptable carriers that may be used are described in the *Handbook of Pharmaceutical Excipients*.

Any suitable gelling agent can be used to prepare the gels of the invention. As used herein, the term "gelling agent" includes any natural or synthetic material that will provide the yield point and viscosity defined herein. Examples of gelling agents found in nature are polysaccharides and carrageenans, alginates and agars, guar gum, gelatin, and locust bean (carob) gum. Also synthetic organics such as polyethylene glycols, particularly the ultra-high molecular weight polyethylene glycols, polyvinyl alcohol-boric acid gels, polyacrylamides, crosslinked polyvinylpyrrolidones, and polyacrylic acids can be used.

Some preferred gelling agents include hydroxyethylcellulose hydroxypropylcellulose cross-linked acrylic acid polymers MVE/MA decadiene crosspolymer, PVM/MA copolymer, ammonium acrylates/acrylonitrogens, carboxymethylcellulose and polyvinylpyrrolidone. It is preferred that the gelling agent comprise between about 0.5% to about 10% by weight with respect to the total weight of the composition.

Film forming polymers are selected from hydroxyethyl cellulose, hydroxypropyl cellulose, hydroxypropylmethyl cellulose (HPMC), hydroxyethyl methyl cellulose, polyvinyl alcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, or chitin and chitosan, alone or in combination, and a bioadhesive polymer selected from polyacrylic acid, polyvinyl pyrrolidone, or sodium carboxymethyl cellulose, alone or in combination.

If anionic hydrophilic polymers are utilized for enhancing viscosity, the overall polymer negative charge may electrostatically attract and accumulate the cationic LAE biocide and a greater concentration of LAE will then be needed to provide biocidal efficacy comparable to the utilization of a neutral or cationic water-soluble polymer. Thus, preferred water soluble polymers are neutral in charge, such as hydroxyethylcellulose, hydroxypropylcellulose, hydroxypropylmethylcellulose, guar, hydroxypropylguar, hydroxypropylmethylguar, poly(ethylene oxide), and poly(N-vinylpyrrolidone), or cationic in charge, such as cationic chitosans, cationic cellulosics, and cationic guar. Chitosan polymers may also enhance the antimicrobial behavior of the antimicrobial composition. More preferred hydrophilic polymers comprise hydroxypropylmethylcellulose, hydroxypropylcellulose, hydroxypropylguar, hydroxymethylchitosan, poly(ethylene oxide), N-[(2-hydroxy-3-trimethylammonium)-propyl]chitosan chloride, with hydroxymethylpropylcellulose being most preferred.

Chelating agents enhance the susceptibility of bacteria and other organisms to the biocidal effects of the antimicrobial agent, thus rendering a wound care solution or device containing a chelating agent more effective in combating infection. Additionally, chelating agents deactivate matrix metalloproteases (MMPs), enzymes that can impede tissue formation and healing by breaking down collagen. MMPs are often found at elevated levels in chronic wounds. Chelating agents bind to zinc ions, which are necessary for MMP activity, disrupting the MMP, causing deactivation, and thus facilitating healing.

The chelating agent is selected from any compound that is able to sequester monovalent or polyvalent metal ions. The cations of the chelating agent are more preferably disodium, trisodium or tetrasodium salts of EDTA, and most preferably disodium EDTA and trisodium EDTA.

The concentration of chelating agent can range from 0.0025 to 1.0 wt %, or from 0.005 to 0.5 weight %, or from 0.0075 to 0.15 weight % and can also be any specific wt % found within this range.

Applications

Potential applications for the compositions of the instant invention include the following: water treatment, potable water, waste water, the inside of pipes carrying either potable or non-potable water or other liquids, flushes for pipes carrying either potable or non-potable water or other liquids, food processing equipment and surfaces, drains, drilling equipment and drilling processes.

Compositions of this invention can be used for many applications, e.g. to penetrate biofilm and/or to kill pathogenic and other microbials in conduits, tubes, etc. used in the dental office, hospital, medical facilities, household, or industry. Non-limiting examples of applications for this invention include antimicrobial products, household products and cleaners, fabric detergents, dish detergents, cleansers, soaps, bubble baths, disinfectants, deodorizers, human and animal foods, food products, beverages, preservative compositions, antimicrobial packaging, pharmaceutical products, medical devices, e.g. catheters, wound dressings, ophthalmic uses, contact lenses and storage containers, cosmetics, feminine hygiene compositions, vaginal douches, infant care products, antimicrobial soaps, hand sanitizers, deodorants, antiperspirants, anti-microbial coatings, dental compositions, toothpastes, mouth rinses and washes, oral swabs and sponges, lipsticks, dental appliances and devices, skin swabs, medications, athlete's foot treatments, cold sore treatments, herpes virus treatments, medicated chewing gums, wound care compositions, dermatological compositions, acne treatments, skin conditioners, skin moisturizers, anti-wrinkle formulations, skin whiteners sunscreens, tanning lotions, hair products, shampoos, shower gels, bubble baths, conditioners, shaving creams, spermicides. Also included are microbial-resistant fabrics and apparel, antimicrobial condoms, surgical gowns, microbial-resistant hospital equipment, anti-microbial paper products, animal care products, antimicrobial plastics, antimicrobial plastic devices, rubbers and other fabrication materials, appliances with antimicrobial constituents or coatings, etc. Activity against gram negative organisms is increased if the pH is about 5.0 lower. Other incipients to enhance antimicrobial activity against gram negative organisms would be the addition of organic acids, e.g. lactic, citric, etc. and small amounts of EDTA, e.g. about 25-50 ppm.

Additionally, compositions of the invention can also be added to articles from where it can release the compositions of this invention. Generally where added to food packaging, the amounts of composition needed to effect food preservation would be higher than the amount needed when incorporated directly into food. Typically, from about 100 ppm to about 5% by weight of the food packaging food products would be used. Also the compositions of the instant invention can be used to coat and/or be added to human or animal food, e.g. kibble.

Additionally, plastics and miscellaneous products can be coated and/or impregnated with or used to deliver the compositions of the invention, including: medical items, thermometers, catheters, surgical sutures, blood lines, implants, bandages, surgical dressings, surgical apparel, respirators, fluid-dispensing tubing; drug and cosmetic packaging, eating utensils shower curtains; bath mats; sponges; mops; toilet seats, rubber gloves; contact lenses; hearing aids; shelving paper; carpet pads; pool covers; animal bedding and cat litter; computer covers and computer keys; doorknobs; tampons and sanitary napkins; adult novelties; sexual aids; sex toys; pregnancy barriers; dental chairs; dryer sheets; dishcloths; paints and coatings; deodorizing liquids, solids, sprays, gels and powders; filters; foams; hair brushes; combs; diaper rash preventer; plasma bag treatment; disposable glove treatment; additive to pasteurized cow milk; additive to blood sample tubes to inactivate HIV, HCMV, and other viruses (safety measure for lab technicians and healthcare providers); additives for condoms, band-aids, or bandages; additive for paint; or animal or plant treatment for microbial infections; animal chew toys, children chew toys, children floating toys, e.g. "rubber ducky", animal and pet food coatings and ingredients, and the like.

Additionally, fibers and fabrics can be coated and/or impregnated with the compositions of the invention, including natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; paper, non-woven fabric, knitted fabric, woven fabric, brick, stone, plastic, polymer, latex, metal, tile, walls, floors, gurneys, tables, or trays; shoes and the like. Regarding the use of ML types and SL types into food packaging or other plastic or polymer films, ML and SL types have outstanding thermal melt stability during melt processing, e.g. in extrusion, injection molding, blow molding, or the like.

Cleaning products can usefully incorporate the compositions of the invention for the purposes of sanitizing or deodorizing surfaces. Typically, the compositions would be added to aqueous cleaning formulations in concentrations between about 100 to about 2000 ppm. Other cleaning agents can be added at the concentrations needed to make the products effective which will depend on usage concentration. Most cleaning formulations contain surfactants. As mentioned previously, virtually all nonionic, amphoteric and cationic surfactants are generally compatible with the enhanced combinations of the invention. Most anionic surfactants will cause the Na-long chain alkanoyl dibasic amino acid alkyl ester salts to precipitate from solution. One advantage of using SL/ML types in combination is that there is no interaction with cationic or anionic species, so the possibility of more stable systems can be realized.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the spirit and scope of the invention encompassed by the appended claims.

Data Generation and Methodology

Ingredients were chosen for highest purity. Sucrose monolaurate was obtained from Mitsubishi Kagaku, RYOTO Sugar Ester (Food grade) L-1995 (90% monoester). LAE-HCl solid (>89% purity) was obtained from A&B Ingredients Inc., Fairfield, NJ Glycerol monolaurate was obtained from Colonial Chemical (90% monoester, 1 position).

Biofilm Porcine Explant Model

The porcine explant model used in the examples of the specification is fully described by Phillips et al. (Wounds International, Vol 1, Is. 3 May 2010). Briefly, the ex vivo model of biofilm on porcine skin explants consisted of 12-mm biopsied explants (3-4 mm thick) prepared from freshly harvested, shaved and cleaned porcine skin. The mechanically created 'wound bed' was 3 mm in diameter and approximately 1.5 mm in depth. The 'wound bed' of the explants was inoculated with early-logarithmic (log)-phase *Pseudomonas aeruginosa* biofilm ("PA01") suspension culture ($10^6$ CFU) and cultured at 37° C. with 5% $CO_2$ and saturated humidity until biofilm maturity was achieved. Typically day 3 for the Examples. An explant thus treated serves as the "total" bacterial count. Some explants were submerged in TSB media containing 200 µg/ml gentamicin for 24 hours to kill planktonic PAO1 and to generate the "biofilm" bacterial count. In yet another set of explants, the explants were treated with compositions of the disclosed invention for 24 hours. The bacterial load of the explants was determined in each of the assays of this study as follows: each explant was aseptically placed into a 15-ml sterile tube (on ice) containing cold 7-ml sterile phosphate-buffered saline (PBS) with 5 µl/l Tween-80. The explants in the tubes were sonicated. Serial dilutions of the bacterial suspension were plated in triplicate on TSA plates and incubated overnight at 37° C. with 5% $CO_2$ and saturated humidity. Colonies were counted from the plates to determine the CFU/ml of the sonicated explant bacterial suspension. The following examples were tested according to the Phillips et al. ex vivo model protocol. The accuracy of the test is ±1 log reduction.

Without being bound by theory it is suggested that the test involves killing of planktonic bacteria that recolonize a debrided wound bed as well as expansion of any biofilm bacteria that were not killed or removed by previous treatment or debridement. In wound healing, many times the wound is subjected to debridement which is a mechanical scraping of the wound surface to open up the biofilm surface. This is painful for many patients and also can remove healthy cells. Furthermore, the ability of a formulation to kill mature biofilm without killing all the wound cells is the most valuable clinical property of a wound treatment. The instant invention formulation also kills planktonic bacteria so it would be predicted to prevent reconstitution of a biofilm after initial debridement and treatment.

EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

The following abbreviations may be found throughout the Examples and Figures: "LAE HCL" is $N^\alpha$ C8-C16 alkanoyl-L di-basic amino acid —C1-C4 alkyl ester being $N^\alpha$-lauroyl-L-arginine-ethyl ester HCL salt; "ML" is monolaurin; "SL" is sucrose laurate; "HPC" is Dow Methocell™ K4M hydroxypropyl cellulose; "TEC" is Triethyl citrate; "CDM" is Croda Arlasilk™ CDM Sodium Coco PG-dimonium Chloride Phosphate phospholipid; "PG" is propylene glycol; "DW" is deionized water; "MIC" is Minimum Inhibitory Concentration; CFUs is colony forming units; Avg is average; ppm is parts per million; Std Dev is standard deviation.

Example 1

FIG. 1A provides the formulation of 4 different compositions that were tested in the ex vivo porcine skin explant model as described above. The results were measured as colony forming units (CFUs) as follows: Total, an average $1.20 \times 10^8$ (Std Dev $7.85 \times 10^7$); Biofilm, an average $1.12 \times 10^7$ (Std Dev $5.45 \times 10^6$); Treatment #1, an average $7.28 \times 10^1$ (Std Dev $6.35 \times 10^1$); Treatment #2, an average $0.00 \times 10^0$ (Std Dev $0.00 \times 10^0$); Treatment #3, an average $1.74 \times 10^4$ (Std Dev $2.00 \times 10^4$); Treatment #4, an average $3.63 \times 10^2$ (Std Dev 132.7222). These results are also shown in a bar graph in FIG. 1B. Three samples give >4 log reduction which is clinically significant. Sample #2 gives complete kill (7 log reduction).

Example 2

Figures 2A, 2B:
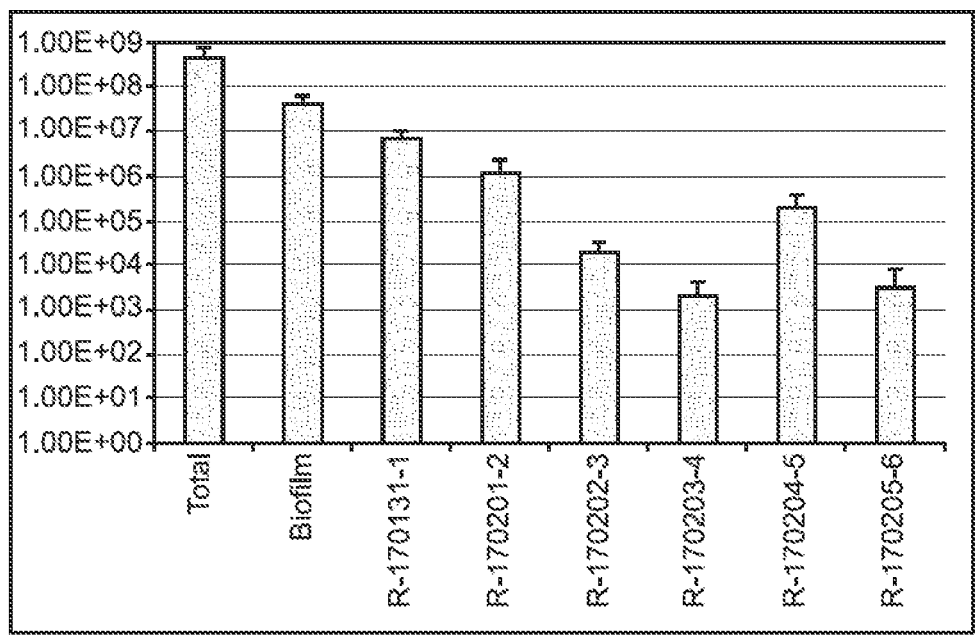
FIG. 2A-B depicts the formulas tested and results after treatment with the compositions of the present invention according to Example 2.

FIG. 2A lists the formulations tested, R-170131-1 through R-170131-6. The results were measured as colony forming units (CFUs) as follows: Total, an average $4.71 \times 10^8$ (Std Dev $2.94 \times 10^8$); Biofilm, an average $4.55 \times 10^7$ (Std Dev $2.32 \times 10^7$); Treatment #R-170131-1, an average $7.47 \times 10^6$ (Std Dev $3.68 \times 10^6$); Treatment #R-170131-2, an average $1.28 \times 10^6$ (Std Dev $1.13 \times 10^6$); Treatment #R-170131-3, an average $1.80 \times 10^4$ (Std Dev $1.21 \times 10^4$); Treatment #R-170131-4, an average $1.98 \times 10^3$ (Std Dev $2.08 \times 10^3$); Treatment #R-170131-5, an average $2.00 \times 10^5$ (Std Dev $1.73 \times 10^5$); Treatment #R-170131-6, an average $3.09 \times 10^3$ (Std Dev $5.53 \times 10^3$). FIG. 2B represents this data as a bar chart of the log CFUs remaining after the treatment. Several samples give >2 log reduction which is clinically significant. Samples R-170203-4 and R-170205-6 give >4 log reduction.

Example 3

Figures 3A, 3B:
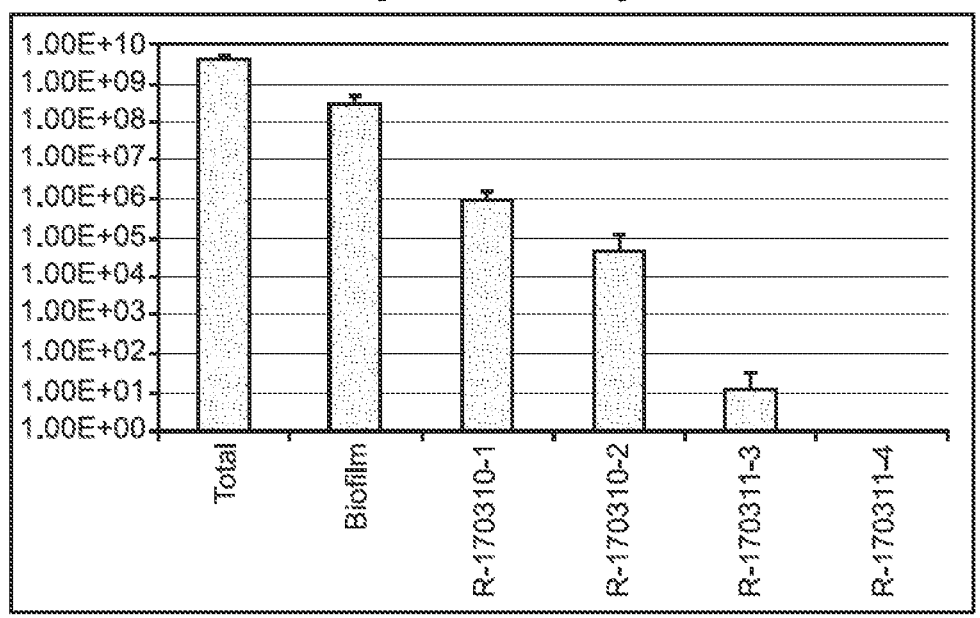
FIG. 3A-B depicts the formulas tested and results after treatment with the compositions of the present invention according to Example 3.

FIG. 3A lists the formulations tested. The results were measured as colony forming units (CFUs) as follows: Total, an average $4.53 \times 10^9$ (Std Dev $3.42 \times 10^8$); Biofilm, an average $2.80 \times 10^8$ (Std Dev $1.73 \times 10^8$); Treatment #R-170310-1, an average $9.40 \times 10^5$ (Std Dev $7.58 \times 10^5$); Treatment #R-170310-2, an average $4.89 \times 10^4$ (Std Dev $7.95 \times 10^4$); Treatment #R-170310-3, an average $1.25 \times 10^1$ (Std Dev $2.50 \times 10^1$); Treatment #R-170310-4, an average $0.00 \times 10^0$ (Std Dev $0.00 \times 10^0$).

FIG. 3B is a bar chart of this data and demonstrates that all four solutions reduced biofilms at clinically significant levels, but #R-170310-3 produced >7-log reduction and #R-170310-4 totally eliminated the biofilm and planktonic bacteria.

Example 4

Figures 4A, 4B:
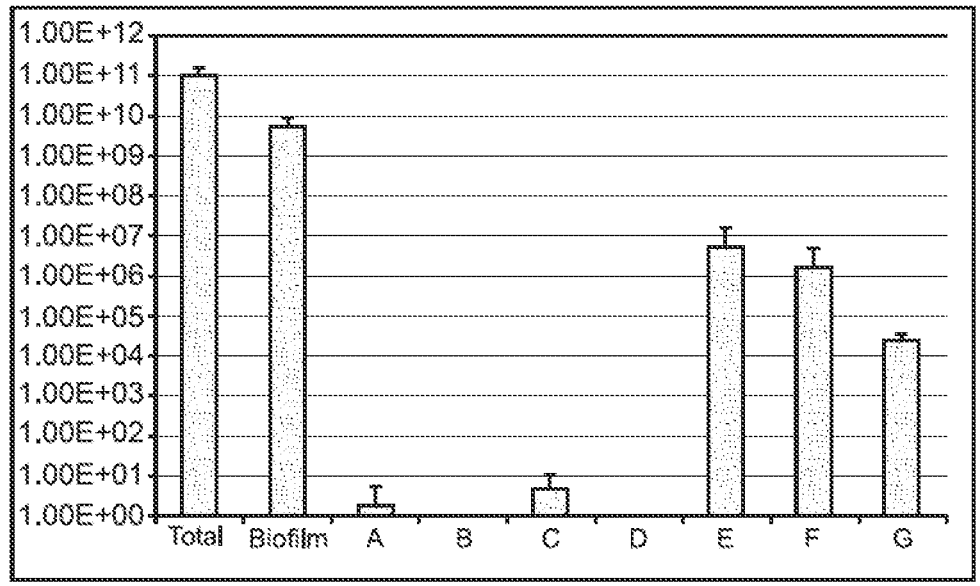
FIG. 4A-B depicts the formulas tested and results after treatment with the compositions of the present invention according to Example 4.

FIG. 4A lists the formulations tested. The results were measured as colony forming units (CFUs) as follows: Total, an average $9.62 \times 10^{10}$ (Std Dev $6.08 \times 10^{10}$); Biofilm, an average $5.69 \times 10^9$ (Std Dev $2.99 \times 10^9$); Treatment A, an average $1.67 \times 10^0$ (Std Dev $3.33 \times 10^0$); Treatment B, an average $0.00 \times 10^0$ (Std Dev $0.00 \times 10^0$); Treatment C, an average $5.00 \times 10^0$ (Std Dev $6.38 \times 10^0$); Treatment D, an average $0.00 \times 10^0$ (Std Dev $0.00 \times 10^0$); Treatment E, an average $5.38 \times 10^6$ (Std Dev $1.05 \times 10^7$); Treatment F, an average $1.51 \times 10^6$ (Std Dev $3.01 \times 10^6$); Treatment G, an average $2.49 \times 10^4$ (Std Dev $1.07 \times 10^4$). FIG. 4B is a bar chart of the log CFUs remaining after the treatment.

FIG. 4B show that all seven formulations reduced biofilms, and all seven gave clinically significant results. Also samples A and C produced 9-log reduction and samples B and D totally eliminated the biofilm. The data of Example 4 demonstrate that a combination of two of the three active ingredients (LAE, ML, or SL) will penetrate and kill biofilm bacteria in a clinically significant level. The data demonstrate that a combination of at least two of the three ingredients in the instant invention, i.e. LAE, ML, and SL, will produce clinically significant biofilm penetration and bacteria kill when tested in the Phillips ex vivo test.

Example 5

Figures 5A, 5B:
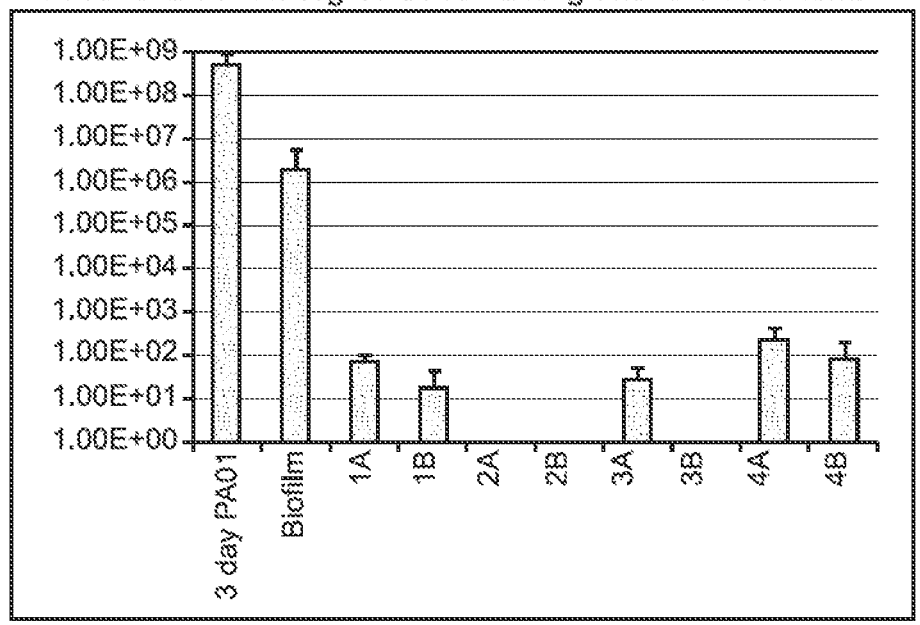
FIG. 5A-B depicts the formulas tested and results after treatment with the compositions of the present invention according to Example 5.

FIG. 5A lists the content of four formulations. Each formulation was treated for 24 hr, then analyzed for samples 1,2,3,4 A. For samples 1,2,3,4 B, explants are treated as in A and then flipped over and immersed again; recovery was in 24 hours, no debridement.

The results were measured as colony forming units (CFUs) as follows: Total, an average $4.37 \times 10^8$ (Std Dev $5.49 \times 10^8$); Biofilm, an average $1.93 \times 10^6$ (Std Dev $2.83 \times 10^6$); Treatment #1A, an average $7.00 \times 10^1$ (Std Dev $3.00 \times 10^1$); Treatment #1B, an average $1.67 \times 10^1$ (Std Dev $2.08 \times 10^1$); Treatment #2A, an average $0.00 \times 10^0$ (Std Dev $0.00 \times 10^0$); Treatment #2B, an average $0.00 \times 10^0$ (Std Dev $0.00 \times 10^0$); Treatment #3A, an average $2.67 \times 10^1$ (Std Dev $2.52 \times 10^1$); Treatment #3B, an average $0.00 \times 10^0$ (Std Dev $0.00 \times 10^0$). Treatment #4A, an average $2.27 \times 10^2$ (Std Dev $1.91 \times 10^2$); Treatment #4B, an average $8.33 \times 10^1$ (Std Dev $1.12 \times 10^2$). FIG. 5B is a bar chart of the log CFUs remaining after the treatment. The formulations of Example 5 produce hydrogel like consistencies.

In Examples 1-5, the data show that varying amounts of LAE, ML, and SL produce clinically significant results, i.e. >2 log reduction. Propylene glycol may aid in solubilization of the ML, and help to penetrate the biofilm.

In Example 5, Sample 2 has the best penetration and kill resulting in >6 log reduction. The result is greater than 99.9999% kill. Sample 3 gave the second best results. This resulted in >4 log drop or 99.99% kill.

The absence of any LAE-HCl in sample #2 clearly shows that the combination of ML and SL are responsible for the penetration of the biofilm and reduction in CFUs. This was also demonstrated in Examples 4 and 5. The levels of the three main ingredients are also much lower in Example 5 when compared to Examples 1 and 4.

Inorganic nitrates can be added as a salt to increase the amount of NO if a reducing sugar is present like sucrose, glucose or sucrose laurate (SL). Triethyl citrate ("TEC") can act as an inhibitor of esterases and can act as a synergist to enhance and prolong the antibacterial activity of both LAE-HCl, ML, and SL.

Example 6

In the previous biofilm testing in Examples 2 and 4, it was unanticipated that a combination of LAE and SL w/o ML reduced or killed both planktonic and biofilm bacteria in the Phillips et al. ex vivo test. Also in Example 4 it was unanticipated that a combination of SL and ML w/o LAE reduced or killed both planktonic and biofilm bacteria. Further testing was performed to show the relationship between LAE and SL. Because the combinations of LAE/SL and SL/ML were also active on planktonic bacteria alone, this would support potential uses for these two combination of LAE/SL or SL/ML as preservatives, e.g. in food, personal care, or cosmetic applications. Example 6 demonstrates combinations of SL/ML show that these two combinations both have activity using time kill/recovery as well as Minimum Inhibitory Concentration (MIC) testing.

Time-Kill Kinetics Test is a method of testing Antimicrobial Efficacy also known as the "suspension tests or suspension time kill analysis", determines the time required by the antimicrobial agent to kill the challenge test microorganism. This test is utilized in microbiological studies to assess a test article's in vitro antimicrobial activity in relation to time. The test essentially perform the following steps: the undiluted and/or diluted test compound is introduced to a particular test bacteria at time zero. This mixture is grown at a set temperature and at specified time intervals, samples are taken out of the inoculum, put into a neutralization buffer, and then the microbe population is enumerated. The resulting data for the Time-Kill test is typically presented graphically, where the colony counts for each antimicrobial agent is plotted against the concentration tested at each time point when the subcultures were performed (usually at 0, 4, 8, 12, and 24 hours). Generally, in a Time-Kill test, a 3-$\log^{10}$ reduction is considered the minimum level that would indicate a product has significant killing activity against a particular test microorganism. In contrast, in the minimal bactericidal concentration (MBC) test, bactericidal activity is defined as a 99.9% or greater killing efficacy at a specified time.

Time kill and MIC values of various mixtures of sucrose laurate and glyceryl monolaurate (monolaurin) on *Staphylococcus aureus* and *Candida alibans* MIC values were determined and are shown in FIGS. 6A and B. ML may be solubilized in propylene glycol (PG), or DMSO. The use of DMSO is well documented in the literature as a solubilizing agent. FIGS. 6A and 6B provide the wt % of the active ingredient of each formulation. Samples in FIG. 6A were tested at 100 ppm each; recovery was at 24 hours. In FIG. 6A samples were supplied at 1 wt % (active ingredient) and solubilized in distilled water with 5% propylene glycol ("PG"). In FIG. 6B samples were supplied at 1 wt % and solubilized in PG. All of the above solutions were conditioned at about 40-45° C. prior to testing and then incubated at 35° C.

In FIG. 6A, the time kill data demonstrates that the combination of 50 wt % SL and 50 wt % ML gives higher log reduction than that of 100 wt % ML. At the data point of 25 wt % SL/75 wt % ML, the log reduction indicates a trend for enhanced biocidal activity. Because the ML was solubilized in FIG. 6A using 95 wt % DW and 5 wt % PG, the slight difference between the average log reduction of 50/50 wt % SL/ML being 2.6 and the average log reduction of 25/75 wt % SL/ML being 1.8 can be explained by the lower solubilizing effect of the SL. Specifically, with an increase of ML from 50 to 75 wt %, we would expect that the log reduction would be similar. This slightly lower average log reduction shows a trend in the enhancement of ML alone. Using only 5% PG to solubilize the 100% ML sample, the PG has not completely solubilized the ML. However in the 50/50 and 25/75 wt % SL/ML samples, the SL contributes to the solubilization of the ML.

In FIG. 6B, 1 wt % ML and 1 wt % SL were supplied as solubilized in PG. In FIG. 6B, the MIC data of combinations of ML and SL show a similar trend as the results in FIG. 6A in the ratios of from 75 wt % ML:25 wt % SL to 25 wt % ML:75 wt % SL all show a degree of enhancement. SL has been reported in the literature to have very high MIC values when tested alone. This data shows that SL enhances the antimicrobial activity of ML possibly through improved solubilization with or without PG. This effect is also shown in the results in Experiments 4 and 5.

Example 7

Example 7 demonstrates the effect of combining sugar esters of fatty acids with Na-long chain alkanoyl dibasic amino acid alkyl ester salts. MIC values of various mixtures of $N^\alpha$-lauroyl arginine ethyl ester HCl salt and sucrose monolaurate in preventing the growth of *Candida alibicans* were determined. In FIG. 7, the MIC data of combinations of SL and LAE are identical to that of 100 wt % LAE. In comparing ratios of wt % of SL to wt % of LAE, ratios from 2:1 to 1:2 show enhancement compared to 100 wt % LAE.

Example 8

In Example 8, different pathogens were tested for MIC (Minimum Inhibitory Concentration) with formulations that comprise combinations of LAE and SL. In the previous biofilm testing in Examples 2 and 4, the combination of LAE and SL without ML reduced or killed both planktonic and biofilm bacteria. FIG. 8A-B shows the results of further testing with LAE and SL. In FIGS. 8A and 8B the active ingredients LAE and SL were solubilized in DW as indicated and were tested. FIG. 8A reports MIC combination of LAE and SL tested on *Candida albicans* fungi in duplicate and for gram positive *S. aureus*. FIG. 8B reports MIC on combinations of LAE/SL exposed to *S. epidermidis*.

In FIG. 8A, ratios of LAE/SL from 25 wt % LAE/75 wt % SL to 75 wt % LAE/25 wt % SL have similar MIC (minimum inhibitory concentration) values. This indicates an enhanced relationship regarding antimicrobial performance for various levels of LAE. Noted are that the levels of 100 wt % SL alone have much higher MIC values than LAE or combinations of LAE/SL.

In FIG. 8B, ratios of LAE/SL solubilized in DW from 40 wt % LAE/60 wt % SL to 60 wt % LAE/40 wt % SL have similar MIC values tested against *S. epidermidis*. This indicates an enhanced relationship regarding antimicrobial performance for various levels of LAE and confirms the data in FIG. 8A. Noted are that the levels of 100 wt % SL alone have much higher MIC values than LAE or combinations of LAE/SL. This high MIC of SL is in agreement with several publications.

It is well known that LAE and ML both have activity against pathogens separately. However ML does not have similar broad activity against all pathogens that LAE does. Using combinations of LAE/SL and of SL/ML show improved activity using lower level of ML with SL, while SL alone has very low activity. Similarly performance of lower levels of LAE alone can be improved with SL. This provides an advantage in cost performance basis as LAE is many times more expensive than cosmetic versions of SL or other sucrose fatty acid monoesters.

As stated above, while the present application has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details of the illustrative examples shown. Departures may be made from such details and examples without departing from the spirit or scope of the general inventive concept.

The invention claimed is:

1. A composition having an active ingredient comprising:
   a combination of an effective amount of a salt having a cation Nα C8-C16 alkanoyl-L di-basic amino acid —C1-C4 alkyl ester and an anion selected from the group consisting: of halide, nitrite, nitrate, linoleate, linolenate, laurate, oleate, phenolate, polyphenolate, carboxylate, hydroxycarboxylate, hyaluronate, antibiotic anion, resveratrol, and an amino acid present in an amount between about 0.025 wt % to about 10 wt % and
   an effective amount of a sugar ester of a fatty acid present in an amount between about 0.075 wt % to about 30 wt %, and
   the composition optionally comprising one or more of:
      a solvent being present in an amount from about 5 wt % to about 99.9 wt %; or
      a thickener or carrier or gelling agent being present in an amount from about 1.0 wt % to about 10.0 wt %; or
      an esterase inhibitor being present in an amount from about 0.05 wt % to about 5 wt %; or
      a hydrogel having a three-dimensional hydrophilic polymer network,
   wherein the active ingredient of the composition kills or inhibits planktonic bacteria or fungi and penetrates the biofilm matrix and kills or inhibits biofilm bacteria or fungi.

2. The composition of claim 1, wherein the application of the composition to a surface or product results in a greater than 2 log reduction in amount of bacteria or fungi on the surface or product compared to an untreated surface or product.

3. The composition of claim 1, wherein the sugar ester of a fatty acid being sucrose laurate.

4. The composition of claim 1, wherein the sugar ester of a fatty acid comprises 90% monoester.

5. The composition of claim 1, wherein the solvent being at least one of: water, 1,2-propylene glycol or 1,3-propylene,m glycol, 1,2-pentanediol, sorbitol, glycerol, xylitol, polyethylene glycol, polypropylene glycol, butylene glycol, pentylene glycol, hexylene glycol.

6. The composition of claim 1, wherein the thickener or carrier or gelling agent being at least one of: a polymer, a hydrocolloid, an acrylate, an acrylamide, a carboxylated cellulose, lecithin, poly(lactic-co-glycolic acid) (PLGA), polymeric ethers, polymeric aliphatic alcohols, polyalkoxylated alcohols, naturally occurring high molecular weight substances such as sodium alginate, gums, xanthan gum, gum tragacanth, starch, collagen aluminum silicate, quince seed extract, semi-synthetic high molecular substances such as methyl cellulose, carboxymethyl cellulose, hydroxyethylcellulose, hydroxypropylcellulose, hydroxypropylmethyl cellulose (HPMC), soluble starch and cationized cellulose, synthetic high molecular substances such as carboxyvinyl polymer and polyvinyl alcohol, arabic gum, carbomer, polyethylene oxide, poloxamer.

7. The composition of claim 1, wherein the esterase inhibitor being at least one of: triethyl citrate, trimethyl citrate, or zinc glycinate.

8. The composition of claim 1, wherein the hydrogel being at least one of: polyvinyl alcohol, polyvinylpyrrolidone, polyethyleneimine, polyacrylic acid, polyhydroxyethyl-methacrylate, polyvinyl alcohol-glycine co-polymer, or polyvinyl alcohol-lysine co-polymer.

9. The composition of claim 7, wherein a benefit agent is solubilized in the hydrogel.

10. The composition of claim 8, wherein the benefit agents is an antibiotic, an antimicrobial, or a drug.

11. A composition having an active ingredient comprising:
   a combination of an effective amount of a salt having a cation Nα C8-C16 alkanoyl-L di-basic amino acid —C1-C4 alkyl ester and an anion selected from the group consisting: of halide, nitrite, nitrate, linoleate, linolenate, laurate, oleate, phenolate, polyphenolate, carboxylate, hydroxycarboxylate, hyaluronate, antibiotic anion, resveratrol, and an amino acid present in an amount between about 0.025 wt % to about 10 wt %;
   an effective amount of a sugar ester of a fatty acid present in an amount between about 0.075 wt % to about 30 wt %, and
   a poloxamer as a thickener or carrier or gelling agent that is present in an amount from 0.2 wt % to 75 wt %
   the composition optionally comprising one or more of:
      a solvent being present in an amount from about 5 wt % to about 99.9 wt %; or
      a thickener or carrier or gelling agent being present in an amount from about 1.0 wt % to about 10.0 wt %; or
      an esterase inhibitor being present in an amount from about 0.05 wt % to about 5 wt %; or
      a hydrogel having a three-dimensional hydrophilic polymer network,
   wherein the active ingredient of the composition kills or inhibits planktonic bacteria or fungi and penetrates the biofilm matrix and kills or inhibits biofilm bacteria or fungi.

* * * * *